(12) United States Patent
Saffie-Siebert

(10) Patent No.: US 9,132,083 B2
(45) Date of Patent: Sep. 15, 2015

(54) DELIVERY SYSTEM COMPRISING A SILICON-CONTAINING MATERIAL

(75) Inventor: Roghieh Saffie-Siebert, Belfast (GB)

(73) Assignee: SISAF Ltd. (GB)

( * ) Notice: Subject to any disclaimer, the term of this patent is extended or adjusted under 35 U.S.C. 154(b) by 541 days.

(21) Appl. No.: 13/387,766

(22) PCT Filed: Jul. 30, 2010

(86) PCT No.: PCT/GB2010/001456
§ 371 (c)(1),
(2), (4) Date: Jan. 30, 2012

(87) PCT Pub. No.: WO2011/012867
PCT Pub. Date: Feb. 3, 2011

(65) Prior Publication Data
US 2012/0128786 A1    May 24, 2012

(30) Foreign Application Priority Data

Jul. 30, 2009  (GB) .................................. 0913255.6

(51) Int. Cl.
| A61K 8/25 | (2006.01) |
| A61K 33/00 | (2006.01) |
| A61Q 19/00 | (2006.01) |
| A61K 9/00 | (2006.01) |
| A61K 8/02 | (2006.01) |
| A61K 8/55 | (2006.01) |
| A61K 9/51 | (2006.01) |

(52) U.S. Cl.
CPC ............ *A61K 9/0014* (2013.01); *A61K 8/0279* (2013.01); *A61K 8/25* (2013.01); *A61K 8/553* (2013.01); *A61K 9/5115* (2013.01); *A61Q 19/00* (2013.01); *A61K 2800/412* (2013.01); *A61K 2800/413* (2013.01); *A61K 2800/612* (2013.01)

(58) Field of Classification Search
CPC ................. A61K 2800/412; A61K 2800/413; A61K 8/25; A61K 8/553; A61Q 19/00
See application file for complete search history.

(56) References Cited

U.S. PATENT DOCUMENTS

| 5,922,360 | A | 7/1999 | Bronder |
| 6,221,344 | B1* | 4/2001 | Ramin et al. ................... 424/61 |
| 2003/0206949 | A1* | 11/2003 | Parikh et al. ................. 424/465 |
| 2006/0159921 | A1 | 7/2006 | Murthy et al. |
| 2007/0042046 | A1 | 2/2007 | Saffie et al. |
| 2007/0071787 | A1 | 3/2007 | Saffie et al. |

FOREIGN PATENT DOCUMENTS

| AU | 774668 B2 | 4/2001 |
| EP | 1 110 909 A1 | 6/2001 |
| EP | 1110909 A1 | 6/2001 |
| JP | 58-176115 | 10/1983 |
| WO | WO0147807 A1 | 7/2001 |
| WO | WO03101915 A1 | 12/2003 |
| WO | WO2004016551 A1 | 2/2004 |
| WO | WO2004060378 A2 | 7/2004 |
| WO | WO2006136003 A1 | 12/2006 |
| WO | WO2009127256 A1 | 10/2009 |
| WO | WO2010096733 A2 | 8/2010 |

OTHER PUBLICATIONS

Rapuano et al., Journal of Colloid and Interface Science, 1997, 193, 104-111.*
Moulari Brice et al., The Targeting of Surface Modified Silica Nanoparticles to Inflamed Tissue in Experimental Colitis, Biomaterials, vol. 29, No. 34, Dec. 2008, pp. 4554-4560, XP-002608443.
International Search Report Application No. PCT/GB2010/001456, Dated Nov. 26, 2010.
Rapuano et al., J. Colloid and Interface Sci., 193 (1997), 104-111.
L.S. Dent-Glasser et al. J. Chem. Soc. Dalton Trans. (1980) 393.
L.S. Dent-Glasser et al., J. Chem. Soc. Dalton Trans. (1980) 399.
Barel et al., Effect of oral intake of choline-stabilized orthosilicic acid on skin, nails and hair in women with photo-damaged facial skin, Arch Dermatol Res. 297:4 (2005), 147-153.
Barel et al., Effect of oral intake of choline-stabilized orthosilicic acid on skin, nails and hair in women with photo-damaged facial skin, 2005, J. of the Academy of Dermatology, Suppl., 3(52):28.
Luo, D. and Saltzman, W. M., Nonviral gene delivery: Thinking of silica, Gene Therapy, 13 (2006), 585-586.
Ahola, M. et al., Silica xerogel carrier material for controlled release of toremifen citrate, Int. J. Pharm. 195 (2000), 219-227.
Ahola, M. et al., In vitro release of heparin from silica xerogels, Biomat. (2001) 1-8.
Lu J, et al., Mesoporous Silica Nanoparticles as a Delivery System for Hydrophobic Anticancer Drugs, Small. 3 (2007), 1341-1346.
Brown, K.R et al. Seeding of Colloidal Au Nanoparticle Solutions. 2. Improved Control of Particle Size and Shape, Chem. Mater. 12(2000), 306-313.
Bogush, G.H. and Zukoski, C.F., Studies of the kinetics of the precipitation of uniform silica particles through the hydrolysis and condensation of silicon alkoxides, Journal of Colloid and Interface Science, vol. 142:1 (1991), 1-18.
Moulari, Brice et al., The targeting of surface modified silica nanoparticles to inflamed tissue in experimental colitis, Biomaterials vol. 29, No. 34, p. 4554-4560.

* cited by examiner

*Primary Examiner* — Abigail Fisher
(74) *Attorney, Agent, or Firm* — Kramer Levin Naftalis & Frankel LLP

(57) ABSTRACT

A composition comprising nanoparticles of a hydrolysable silicon-contain material for use as a delivery system for a bioactive ingredient, wherein surface of the silicon-containing material is associated with a stabilizing agent which modifies the rate of hydrolysis of the silicon-contain material and/or inhibits the rate of orthosilicic acid polymerization and a method of promoting the controlled release of orthosilicic acid on degradation of a composition comprising nanoparticles of a hydrolysable silicon-contain material, the method involving the treatment of the surface of the silicon-containing material with a stabilizing agent to modify the rate of hydrolysis of the silicon-containing material and/or inhibit the rate of orthosilicic acid polymerization.

24 Claims, 5 Drawing Sheets

__US 9,132,083 B2__

DELIVERY SYSTEM COMPRISING A SILICON-CONTAINING MATERIAL

CROSS REFERENCE TO RELATED APPLICATIONS

This application is the United States national phase filing of the corresponding international application number PCT/GB2010/001456, filed on Jul. 30, 2010, which claims priority to and benefit of GB Application No. 0913255.6, filed Jul. 30, 2009, which applications are hereby incorporated by reference in their entirety.

FIELD OF THE INVENTION

The present invention relates to a composition comprising nanoparticles of a hydrolysable silicon-containing material and a bioactive ingredient, the nanoparticles acting as a carrier in the delivery of the bioactive ingredient.

BACKGROUND TO THE INVENTION

Improved methods for achieving effective delivery of active ingredients to the desired target site remain a goal of the cosmetics, skin care and pharmaceutical industries.

A number of ways of delivering of pharmaceutically active ingredients in a controlled or slow-release manner have been developed. However, little attention has previously been paid to the fate of the carrier material once it has performed its function of delivering and releasing the active ingredient. This invention seeks to provide a new type of delivery system in which a silicon-based carrier material is converted to a beneficial substance following administration.

Topical delivery of active agents presents particular problems due to such factors as the poor stability of most biological compounds, the inability of active agents to penetrate into the deeper skin layers due to their molecular size or other adverse characteristics such as hydrophobicity, and the poor biocompatibility of topical formulations resulting in health concerns.

To enable a wider range of active ingredients to be delivered topically, considerable research has been focused on development of strategies for temporarily disrupting the stratum corneum barrier in a controllable fashion, so that drugs can permeate in sufficient and predictable quantities, thus attaining therapeutic levels. While some techniques such as iontophoresis and ultrasound have been explored as skin absorption enhancers, most effort has centred on identifying non-toxic chemical penetration enhancers that could reversibly interact with the stratum corneum in order to allow greater amounts of drug to permeate the skin. Early attempts to disrupt the barrier used simple solvents or solvent mixtures, surface-active agents and fatty acids. These materials, although capable of increasing the penetration of many chemicals across the skin, were often associated with undesirable side effects linked to their ability to extract or interact with skin components, thereby eliciting an irritation response.

The use of delivery systems has also been investigated. Commonly used delivery systems include relatively viscous fluids such as lotions, creams and gels which can be rubbed into the skin, providing immediate contact with the target region. These vehicles are frequently successfully used for both cosmetic and pharmaceutical compounds. Typically, however, they are unsuitable for delivering active compounds over long periods of time.

In order to create controlled release topical delivery system and other vehicles have been used. Particularly commonly used topical delivery systems utilise lipid based carriers, such as liposomes. However, these carrier systems have a number of drawbacks such as a potentially unstable central core and a limited loading capacity for hydrophobic compounds. They are also unsuitable for delivering substances which are too large or disruptive for phospholipid vesicles and are expensive to produce.

There remains a continuing need for improved delivery systems for topically applied active agents that can protect labile actives such as botanical extracts, desquamating enzymes and the like, and deliver such agents to the skin in active form, while being suitable for formulation into vehicles.

Silicon is an essential trace element for plants and animals. Silicon has a structural role as a constituent of the protein-glycosaminoglycans complexes found in the connective tissue's matrix of mammals, as well as a metabolic role in growth and osteogenesis (silicon favours the process of mineralisation of the bone). Thus, silicon is essential for the normal development of bones and connective tissue. Silica is also known to play an important role in skin health, acting as a collagen and elastin promoter and being involved in anti-oxidative processes in the body. It is implicated in the production of glycosaminoglycans and silica-dependant enzymes increase the benefits of natural tissue building processes.

For medical applications, silicon can be produced as micro- or nanoparticles, which facilitates its administration via a variety of routes such as topical, oral intake, injection or implant. Biodegradable silicon-based particles have also been used for drug targeting. However, the bioavailability of silicon is often limited by poor solubility and organic silicon-containing materials tend to exhibit unacceptably high toxicity, limiting their use in cosmetic, skin care and pharmaceutical applications.

Porous silicon was first discovered by accident in 1956 by Arthur Ulhir Jr. and Ingeborg at the Bell laboratories in US. Fabrication of porous silicon may range from its initial formation through stain-etching or anodization cell using single or poly crystal silicon immersed in hydrofluoric acid (HF) solution. Creating pores in the silicon allows both degradation of material and the loading of active compounds into pores of silicon. The use of porous silicon and porous silica as a carrier for other active compounds has been described (Nonviral gene delivery: Thinking of silica, D. Luo and W. M. Saltzman, Ahola M, Kortesuo P., Kangasniemi I., Kiesvaara J., Yli-Urpo A., Silica xerogel carrier material for controlled release of toremifen citrate. *Int. J. Pharm.* 195 (2000) 219-227. Ahola M., Säilynoja E. S., Raitavuo M. H., Vaahtio M. H., Salonen J. I., Yli-Urpo A U O. In vitro release of heparin from silica xerogels. *Biomat.* (2001) 1-8 Lu J., Liong M., Zink J. I., Tamanoi F., Mesoporous Silica Nanoparticles as a Delivery System for Hydrophobic Anticancer Drugs. *Small.* 2007 Jun. 13.) However, the importance of the degraded product of such carrier systems has not received full attention. In particular, sufficient attention has not previously been paid to ensuring that a silicon-containing carrier system degrades to form the beneficial and bioactive form of silicon, orthosilicic acid, without polymerisation.

The dissolution products of silicon within an aqueous environment are silicic acids. Silicic acid is a general name for a family of chemical compounds of the elements silicon, hydrogen, and oxygen, with the general formula $[SiO_x(OH)_{4-2x}]_n$. Some simple silicic acids have been identified in very dilute aqueous solutions, such as metasilicic acid ($H_2SiO_3$), orthosilicic acid ($H_4SiO_4$, $pK_{a1}=9.84$, $pK_{a2}=13.2$ at 25° C.), disilicic acid ($H_2Si_2O_5$), and pyrosilicic acid ($H_6Si_2O_7$); and further polymerised silicic acids (PolySA), with silica ($SiO_2$) representing the end point of complete polymerisation. The monomeric form of silicic acid, orthosilicic acid (OSA), alternatively known as monosilicic acid, and silica represent opposite sides of the silicon-based reactions with silica representing the energetically favorable form. Concentration and pH determine the direction of reaction and the equilibrium between monomers, polymers and silica:
Low Concentration/High pH High Concentration/Low pH

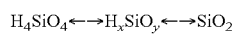

Silicic acids can be considered as buffer molecules. Orthosilicic acid (OSA) is a very weak acid, weaker than, for instance, carbonic acid. It dissociates with a $pK_1$ of 9.84 at 25° C. according to:

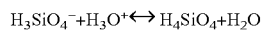

With a pKa around 9.8 silicic acid represents a mixture of ionised and undissociated acids. The ionised species ($H_3SiO_4^-$) can absorb protons from solution raising pH whereas the undissociated species can donate a proton to neutralise hydroxide ions raising pH thereby buffering the solution. It is worth noting this buffering capacity occurs quickly at low concentration. At high concentration, low pH promotes silicic acid to undergo condensation reactions producing dimers ($H_6Si_2O_7$) or higher structures and water. These dimers and higher structures ($SiO_xOH_y$) can dissociate back to monomers or lower structures by absorbing hydroxide. Thereby lowering ph, Likewise these polymerised acids still dissociate at high pH neutralising hydroxide. Thus, polymerised silicic acid can also as a buffer however reactions are considerably slower.

Due to the enthalpy of the dimerisation reaction and subsequent polymerisation reactions at ambient temperatures under biological pH polymerisation generally proceeds

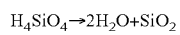

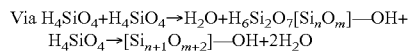

The back reaction is of course possible but is thermodynamically unfavourable requiring pH>13 and heat to return from $SiO_2$ to $H_4SiO_4$.

The reaction of OSA with itself to form silica can be limited by reducing its concentration to the point where two OSA molecules meeting is as likely as a dimer meeting an OH⁻ ion and dissociating. The concentration in limit of a pure solution containing only silicic acid is around $10^{-4}$ Mol·L⁻¹ (Studies of the kinetics of the precipitation of uniform silica particles through the hydrolysis and condensation of silicon alkoxides, *Journal of Colloid and Interface Science*, Volume 142, Issue 1, 1 March 1991, Pages 1-18 G. H Bogush and C. F Zukoski IV) and above this concentration one cannot extract pure OSA as other PolySA species are formed. At higher concentrations, however, orthosilicic acid can be prevented from polymerisation through the addition of other chemical species and method of formulation discussed below.
Kinetics of Dissolution:

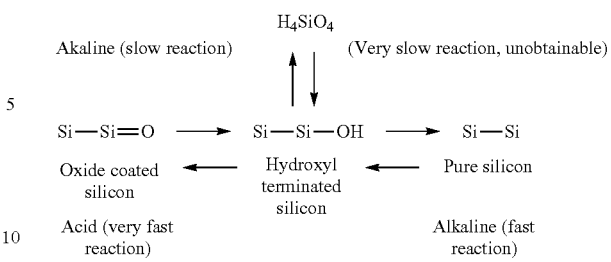

The kinetics of dissolution, ignoring surface area, are dependant on the pH and the availability of reactive species. The main reactive species in the dissolution process is water in its protonated and deprotonated forms. Kinetic data for the rates of reaction in both directions, see Brinker sol-gel science and technology. However the addition of other molecules can create side reactions greatly shifting the equilibrium up to silicic acid or right to silicon oxide (glass) depending on their pKa value this will be discussed further in the particle environment section.

The control of dissolution through adjustment of pH is possible for storage applications, however pH in vivo is tightly controlled by the body. Thus adjustment of dissolution rates through particle size and surface chemistry must be tailored prior to in vivo use. Thus, to increase the rate of dissolution pure, protonated or hydroxylated silicon is preferable. To slow the dissolution of silicon particles a suitable oxide layer thickness will produce a lag in the dissolution profile whilst the oxide layer slowly dissolves. the thickness of this oxide layer will determine the length of the lag period before any water has access to the silicon core.

Care will have to be taken with the manipulation of the silicon surface as binding of drug molecule will be highly dependant on the surface energy. Hydroxylation of the surface will reduce contact angle favouring the binding of polar molecules. Whilst the growth of a surface oxide will increase contact angle favouring the binding of hydrophobic molecules. Thus a combined strategy of size and surface chemistry will be required to obtain control over the level of drug loading and dissolution rate.

The use of silicon oxides in various forms has been proposed as a nutrient for skin and other parts of the human body, such as nails or bones, and in the treatment of bone or joint conditions such as arthritis. The prerequisites for biologically active silicon are its aqueous solubility and its subsequent reactivity towards biomolecules. Silica hydrosolubility depends on the ratio of free OH groups (silanol functional groups) to silicon backbone. Increasing silica complexity results in a reduced ratio of silicon to silanol groups resulting in large macro molecules of poor solubility and reactivity compared to smaller analogues. Thus, the effectiveness of such formulations depends on the ability of silicon to degrade to form OSA, the most biologically active and hence beneficial type of silicic acid. It has been shown that OSA has a high affinity for $Al^{3+}$ ions and enhances their elimination. It can therefore act against the toxic effects of aluminium on bones and brain, especially in neurologic degenerative diseases such as Alzheimer's disease. Formation of metal ion silicic acid salt complexes stabilise OSA in the monomeric form and aid elimination of potentially harmful metal ions from the body.

OSA is a very weak acid which is unstable stable at pH levels lower than 9.5 and quickly precipitates or forms sols or gels which are not very bioavailable for the human body. It is therefore very difficult to prepare highly concentrated (>0.5% silicon) solutions of orthosilicic acid and oligomers. Furthermore, the type of silicic acid produced by a formulation is largely determined by the concentration of silicic acids silicon compounds and the pH of the media in which this dissolution occurs. In order to obtain OSA in vivo, the silicic acid concentration must be tightly controlled.

Although others have considered the potential use of microparticles of silicon-based materials as delivery vehicle for beneficial compounds, the production of high and controlled levels of degraded silicon—especially its bioactive form, ortho silicic acid (OSA) following the degradation of such carrier systems remains difficult to achieve. Previously proposed silicon-based drug delivery systems do not produce and release OSA in a controlled manner and the extent to which the silicic acid remains in the form of OSA has not previously been determined for those formulations. Since many formulations decompose rapidly producing high concentrations of OSA, this could possibly lead to inadvertent poly silicic acid (PolySA) production.

While silica and silicon-based formulation have been used as a carrier system for several applications, polymerisation is a major safety issue if silicon is used as a drug carrier. Previously disclosed delivery systems using all forms of silicon, whether porous, microsilica, nanosilica or silicon dioxide particles, are claimed to undergo dissolution with the particles being degraded to form silicic acid. However, a major problem with known silicon-based delivery systems is that the production and release of OSA is not controllable and, as a result, polymerisation may occur. The particle size distribution of precipitated Si is not homogenous and the silicon structure consists of aggregates and agglomerates. Primary particles of silicon, or silica, become coupled to each other by hydrogen bonds at first into primary agglomerates (aggregates) which, at a further stage, bind to form spatial structures of the secondary agglomerates. This lack of homogeneity of unmodified silica and the particle size growth can be a significant safety issue if the particles are still in the body in the form of silicon particles or silicic acid while releasing the active compounds.

Skincare, cosmetic, pharmaceutical and cosmeceutic compositions comprising stabilised OSA are known. However, such stabilised compositions are not suitable for use as drug delivery systems. For example, the use of bioavailable orthosilicic acid in skin care compositions has been described previously in the literature by Barel et al. (2004): Effect of oral intake of choline-stabilized orthosilicic acid on skin, nails and hair in women with photo-damaged facial skin, *Skin Research and Technology*, 10:1 and Barel et al. (2005): Effect of oral intake of choline-stabilized orthosilicic acid on skin, nails and hair in women with photo-damaged facial skin, *The Journal of the Academy of Dermatology*, Suppl., 3 (52): 28.

The production of OSA outside the body has been studied and the supply of the body with pre-produced OSA solution has been described in JP 58-176115. Concentrated solutions of orthosilicic acid have been produced in which orthosilicic acid is stabilised by a very acid pH that prevents polymerisation by hydrolysing the siloxane bonds Si—O—Si. As the orthosilicic acid is in solution form and not solid or semi-solid particles, it is not able to deliver the active compound in a controlled manner.

Australian patent AU 774668 B2 describes a complex containing biologically assimilable orthosilicic acid in a solid form that is stabilised by complexation to a polypeptide. Such complexes are prepared by hydrolysing a precursor of hydrosilicic acid, such as tetraalkoxysilane, in the presence of an aqueous solution of the polypeptide and then evaporating the water to form a sold complex. Suitable polypeptide stabilizers described in AU 774668, which are capable of stabilising orthosilicic acid, include protein hydrolysates, collagen hydrosylates. Although such complexes are capable of delivering OSA in a biologically assimilatable form that is stable at neutral and physiological pH levels, it does not provide a system that is capable of delivering other beneficial compounds, such as therapeutically active agents.

U.S. Pat. No. 5,922,360 describes stabilized forms of OSA and biological preparations comprising stabilised OSA. In particular U.S. Pat. No. 5,922,360 describes stabilization using a stabilizing agent containing a nitrogen atom with a free electron pair which forms a complex with the silanol groups of the OSA. Suitable stabilizing agents described are quaternary ammonium compounds, for instance tetra-alkyl compounds, wherein each alkyl group contains for instance 1-5 carbon atoms, in particular methyl and ethyl groups, and trialkylhydroxyalkyl compounds, wherein the hydroxy group is preferably methanol or ethanol. Choline, for example in the form of choline hydrochloride, is described as particularly suitable and also an amino acid, such as proline and serine which enhances uptake in the stomach and gives additional stability. The stabilised OSA is prepared by hydrolysing a silicon-containing compounds in water in the presence of the stabilising agent so that OSA complexes with the stabilising agent upon production. International patent application WO 2004/016551 A1 similarly discloses a method for preparing a silicic acid containing extrudate in which a silicon compound is hydrolysed to OSA in the presence of a stabilising agent selected from a quaternary ammonium compound, an amino acid or an amino acid source.

There remains a need for a silicon-based delivery system in which the silicon-containing carrier material reliably degrades to OSA and in which polymerisation of the OSA can be prevented.

SUMMARY OF THE INVENTION

The present invention relates to a delivery system comprising a carrier system made from a solid, hydrolysable, silicon-containing material, said delivery system being able to deliver an active ingredient whilst also providing the benefit of releasing orthosilicic acid as the carrier system degrades at a controlled rate.

In a first aspect, the invention provides a composition comprising nanoparticles of a hydrolysable silicon-contain material wherein surface of the silicon-containing material is linked to or otherwise associated with a stabilizing agent. The stabilising agent controls the rate of hydrolysis of the silicon-containing material to release of OSA and/or stabilizes OSA once formed by inhibiting the rate of orthosilicic acid polymerisation.

It has been found that by associating stabilizing agents to the surface of silicon nanoparticles, a drug delivery system is provided that both provides the controlled release of a biologically active agent and also reliably degrades to form beneficial and bioavailable orthosilicic acid. Moreover, formulations comprising the silicon nanoparticles of the present invention have been found to produce and release OSA at a controlled rate, thus avoiding the release of OSA at concentrations favouring the formation of PolySA. It has also been found that chemical modification of the surface of the nanoparticles can increase the stability of the OSA released upon hydrolysis and hence improve the bioavailability of the silicon. In one embodiment, the invention provides a new type of delivery system in which a silicon-based carrier material is converted to a beneficial substance following administration.

The use of a hydrolysable silicon-containing material as a carrier affords the possibility of targeting and controlling the release of the active ingredient as the silicon-containing material biodegrades following administration, for example within the skin, and the active ingredient dissociates from the carrier and is released, for example into the skin when administered topically. The formulations of the invention enable the dissolution of particles following administration to be released at the same time or faster than the release of active compound. Controlling this process allows OSA to be produced in a manner that avoids subsequent silicic acid polymerisation. It has been found in some embodiments that 100% OSA production is achieved where a silicon to stabilising agent ratio of less than 1 mol/mol, ideally 0.33 or less, depending on the type of stabilising agent used in formulation. It has been found that the presence of 3 or more moles of stabiliser for every 1 mole of silicon is particular advantageous in some embodiments.

In a second aspect, the invention provides a method of promoting the controlled release of orthosilicic acid on degradation of a composition comprising nanoparticles of a hydrolysable silicon-contain material for use as a delivery system for a bioactive ingredient, by treating the surface of the silicon-containing material with a stabilizing agent to modify, for example to inhibit, the rate of hydrolysis of the silicon-containing material and/or inhibit the rate of orthosilicic acid polymerisation.

According to a third aspect of the invention, there is provided a method for preparing the composition of the first aspect of the invention. In particular, there is provided a method of preparing a composition for use as a delivery system for a bioactive ingredient, comprising the step of contacting nanoparticles of a hydrolysable silicon-contain material with a solution comprising a stabilizing agent.

Accordingly to a fourth aspect of the invention there is provided a composition of the first aspect of the invention for use in a method of cosmetic treatment of the human or animal body, for use in a method of treatment of the human or animal body by therapy or diagnosis or for use as a cosmetic. The invention further provides a method for the therapeutic, diagnostic or cosmetic treatment of the human or animal body comprising the step of administering to a composition of the first aspect of the invention comprising an effective amount of a bioactive ingredient.

DETAILED DESCRIPTION OF THE INVENTION

Figure 1:
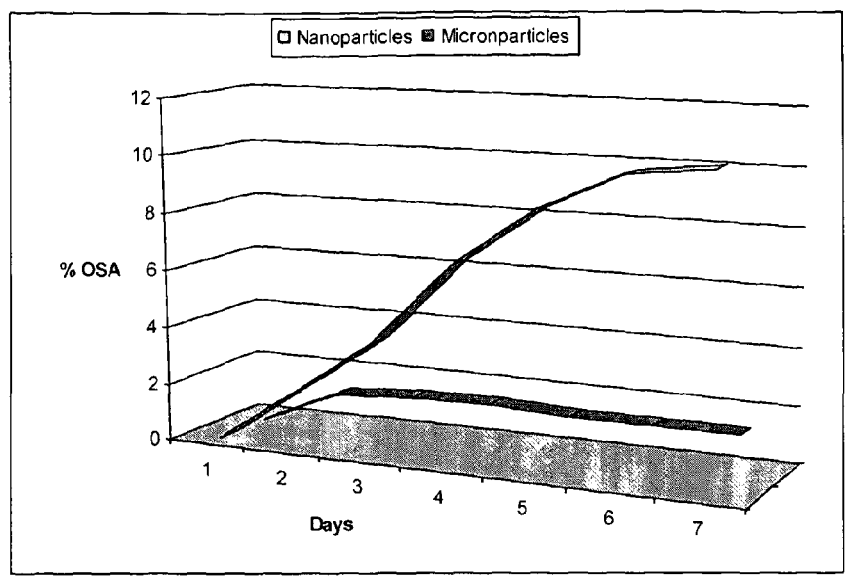
FIG. 1 shows the effect of the particles size on the production of OSA.

In one embodiment, the present invention provides a composition, for example a topical composition, comprising nanoparticles of a hydrolysable silicon-contain material wherein the surface of the silicon-containing material is modified by attachment of a compound which limits the rate of OSA production and stabilizes the silicic acid produced upon hydrolysis of the silicon in its ortho-form. On hydrolysis of the silicon containing material, the OSA molecules produced are stabilized by complexation with the stabilizing compound and are thus prevented from polymerizing.

Degradation to Ortho Silicic Acid

The present invention relates to the realisation that unless the rate of hydrolysis of the silicon containing material is controlled, orthosilicic acid produced will be present at concentrations in which polymerisation is favoured and silicic acid will not therefore be released in its bioavailable and beneficial form. In one embodiment, the surface of the nanoparticles of the composition of the present invention is associated with a stabilizing agent which modifies, for example inhibits, the rate of hydrolysis of the silicon-containing material.

In one embodiment, the rate of hydrolysis of the silicon containing material is modified by the presence of the stabilising agent such that the rate is less than 50% of the rate of hydrolysis of an identical composition without the stabilising agent, preferably less than 30%, especially less than 10%. In one embodiment of the second aspect of the invention, there is provided, a method of promoting the controlled release of orthosilicic acid wherein the rate of hydrolysis is slowed to the levels specified above. By slowing the rate of hydrolysis to a level below that at which OSA is assimilated by the body or removed from the delivery site, for example by diffusion, it has been found that polymerisation can be avoided or at least lessened and the beneficial effects of delivery of OSA to the body can be realised.

In another embodiment the rate of hydrolysis is enhanced by the presence of the stabilising agent such that the rate is greater than the rate of hydrolysis of an identical composition without the stabilising agent.

If a high concentration of OSA in aqueous solution is to be achieved, it is necessary to for a stabilising agent to be present in the solution that inhibits the reaction of OSA with further molecules of OSA that results in a polymerised forms of silicic acid. Therefore, the present invention relates to the realisation that it is advantageous to include in a stabilising agent capable of stabilising OSA in solution in a solid formulation comprising silicon. In particular it has been found that by associating such a stabilising agent with the surface of a composition comprising nanoparticles of a hydrolysable silicon-containing material for use as a drug delivery system, a formulation is provided which inhibits the polymerisation of the OSA produced on hydrolysation of the composition such that substantial levels of the silicic acid produced remains in its beneficial and bioavailable form.

As the monomeric silicic acid degradation product is naturally available in the human body, the use of nanoparticles of hydrolysable silicon-containing material bears a very low risk of toxicity, which is a significant advantage over many other delivery systems. The delivery system according to the invention affords the additional advantage that the carrier decomposes to provide a bioavailable compound which is known to be beneficial. For example, OSA is known to stimulate cellular proliferation and migration in certain cell types, including fibroblasts, endothelial cells and keratinocytes.

Advantageously, the bioavailable orthosilicic acid degradation product of the nanoparticles according to the invention may itself be beneficial as a nutrient for skin, bones, hair, nails, connective tissue, and for the treatment or prevention of bone or joint conditions such as arthritis or osteoporosis.

Stabilizing Agents

The stabilizing agent is a compound that modifies, for example reduces, the rate of hydrolysis of a silicon containing material in an aqueous solution, for example in phosphate buffered saline (PBS), and/or stabilises OSA in such a solution once formed by inhibiting the rate of polymerisation of OSA. Accordingly, the stabilising agent may, for example, be described as agent that promotes the formation of OSA on hydrolysis of a silicon containing material in an aqueous solution, in particular in a commonly used aqueous buffer solutions such as tris or phosphate buffered saline, and/or which inhibits the rate of OSA polymerisation in aqueous solution following hydrolysis of the silicon-containing material. Many such agents are known in the art. Generally, PBS contains the following constituents: 137 mM NaCl, 2.7 mM KCl, 10 mM sodium phosphate dibasic, 2 mM potassium phosphate monobasic and a pH of 7.4. PBS is used for a model of physiological conditions a temperature of 37° C.

As discussed above, silicon hydrolyses to OSA in aqueous media and then subsequently polymerises into molecular entities of various chain lengths and structures, eventually forming water-insoluble silicates. The composition according to the present invention optimises the biodegradation process, so that polymerisation of the OSA formed is substantially suppressed. In this way the degradation product is stabilised and its properties, particularly solubility and viscosity, controlled in order to maximise bioavailability. This is achieved by chemical modification of the nanoparticle surface, the surface being linked to, or otherwise associated with, a stabilising agent. The choice of stabiliser can determine the rate of production of OSA. For example the rate of hydrolysis of silicon to OSA can be increased by associating the surface of the nanoparticles with an amino acid having a negatively charged side chain and/or having more carboxyl groups than amino groups, such as aspartic acid or a lipid with a negatively charged head group such as a phospholipid. Conversely the rate of hydrolysis can be reduced by associating the surface of the nanoparticles with an amino acid having a hydrophobic side chain, such as tyrosine, and/or having a side chain comprising an amino group. Thus, the stabilising agent can be used to tailor the rate of hydrolysis such that a desired rate of OSA production is achieved.

Factors that affect the ability of the stabilising agent to stabilise OSA in solution include:
1—Overall ionic stage in the formulation—in order to form a salt and stabilise OSA the stabilising agent should be positively charged at the pH of silicon dissolution.
2—Effectiveness related to strength of nucleophile, stronger nucleophiles being more effective stabilising agents.
3—The size of the molecule with respect to packing density, smaller molecules that are able to pack more densely are typically more effective stabilising agents— see the data showing that amino acids a generally work better than vitamins.
4—Method of linkage. If you have strong linkage the OSA dissolution is slower and thus less chance of polymerisation.

In the absence of a stabiliser, polymerisation proceeds rapidly with OSA concentrations of over $10^{-4}$M, which corresponds to 9.6 mg/L or 0.48 mg/50 mL. In one embodiment the stabilising agent is capable of stabilising a solution of OSA at concentrations higher than $10^{-4}$M mg/L, for example, a concentration of 0.5 mg/50 mL or more, especially concentration of 0.80 mg/50 mL or more. Advantageously, the stabilising agent is capable of stabilising OSA solutions of 0.90 mg/50 mL or more, for example 0.95 mg/50 mL or more, especially 1.0 mg/50 mL or more.

Advantageously, a stabilizing agent is included in the compositions of the present invention that forms surface linkages to the silicon-containing material. Advantageously, as a result of the linkage of the stabilizing agent to the surface of the silicon-containing material, the rate of hydrolysis of the silicon-containing material to OSA is predictably modified. The presence of the stabilising agent causes changes to the ionic status of the nanoparticle surface and brings about the controlled release of drugs co-formulated within the silicon-based structures themselves.

Advantageously, the stabilizing agent interacts with silanol groups on the surface of the silicon-containing material to form linkages to the nanoparticle surface. Linkages between solid surfaces and stabilising agents may involve the formation of covalent bonds or physical attraction forces including electrostatic and/or van der Waal's forces.

The major effect on the ionic state of the surface of the reacting silicon is more attributable to the presence of the additives, compared to in its absence, rather than their precise concentrations in the formulation and therefore more emphasis is placed on their qualitative effects on OSA release-controlling parameters instead of defining exact limit quantities. Nevertheless, it has been found that the stabilizing effect is enhanced when substantial levels of stabilizing agents are present in the composition.

In one embodiment, the composition comprises at least 5% by weight stabilising agent, for example at least 20 wt %, typically at least 30 wt % and especially at least 50 wt % stabilising agent based on the total weight of the composition. In one embodiment the molar ratio of the stabilising agent to silicon is at least 0.8 to 1, for example at least 1 to 1, typically at least 1.5 to 1. It has been found that a stabilizing agent to silicon molar ratio of at least 2 to 1 is particularly advantageous.

In one embodiment, the stabilising agent is an acid/base and/or nucleophile, such as a salt comprising a carboxylate anion and metal cation, such as sodium ions, the cation of a weak base, or quarterly ammonium cation, which has an effect on the ionisation environment as depicted by pKa and pH. These effects can occur with additives either singly or in combination. It is possible to develop formulations utilising stabilisation agents with $pK_a$ values across the entire range depending on formulation solvent and it is known that formulations at low pH values will result in slower formation of OSA and consequently slower drug release.

It has also been discovered that the polymerisation of OSA and aggregation of particles is due to the formation of uncharged particles. The stabilising agent may be an acid or a base that stabilises OSA by the formation of a salt. Therefore, the main factor for the continuous production of OSA and prevention of aggregation products is the presence of anions to counter balance the charge and stabilise the molecule. Through the functionalisation of the surface or the addition of compounds which act as Lewis bases forming salts with silicic acid the stability of monomeric silicic acid in solution can be enhanced. In one embodiment, the stabilising agent is a Lewis base with a pKa of less that 8.9. such Lewis bases are capable forming and stabilising salt complexes with silicic acid.

The excess of electrons in the formulation increases the ionisation and subsequent interaction with aqueous environments during the process of dissolution, which improves the solubility of silicon. In one embodiment, the stabilizing agent is a base (B) that is capable of forming a salt conjugate of the form $SIO^-BH^+$. Suitable bases typically have a $pK_a$ of 9.84 or above. Stabilizing compounds which have an alkaline character can interact with surfaces of an acidic nature, such as silica. Suitable basic stabilizing agents include sodium hydroxide.

In one embodiment, the stabilizing agent is an alternative ligand that can substitute the Si—OH ligand or Si—H groups on the surface of the silicon-containing materials. Compounds that are suitable for substituting the OH ligand include carboxylic acids (for example, RCOOH, where R is an aliphatic group, especially a $C_{1-10}$alkyl, $C_{1-10}$alkenyl or $C_{1-10}$cycloalkyl group) which bind more strongly to Si in aprotic solvents and can therefore be used replace silanol OH ligands. Examples of other compounds which can react with the surface of silicon are listed below:

| Silicon reacts with . . . | to produce . . . |
|---|---|
| Methanol, R—OH[a] (where R is as defined above) | SiH and Si—OCH$_3$, SiO—R |
| Trimethylchlorosilane or hexamethyldisilazane[b] | Si—OSi(CH$_3$)$_3$ |
| CCl$_4$ or trichloroethylene[c] | Oxidized Si |
| CF$_3$COOH | Si—OCOCF$_3$ |
| Organo-methoxysilane, RSiOCH$_3$ (where R is as defined above) | Si—OSiR |
| N$_2$ or NH$_3$[d] | SiH and Si—NH$_2$ |

Notes
[a]ideal for alkyl grafting on Si; the hydrophobic surfaces capped with a monolayer of long alkyl chains were dramatically stabilized under chemical demands
[b]typical hydrosilylation; can also be employed to different alkenes and alkynes, mediated by the Lewis acid EtAlCl$_2$ or through thermal or photoinduction (white light); hydrosilylation involves covalent modification of alkynes and/or alkenes into vinyl and/or alkyl groups bound to the surface of the Si; different chemical functionalities can be tolerated by these hydrosilylation reactions, including ester, hydroxy, chloro, nitrile and chiral groups
[c]hydrogen can be removed through chlorine but do not lead to halogenation, inducing oxidation instead
[d]nitridation is more efficient in ammonia than in nitrogen; can also terminate Si surface with oxynitride by annealing Si in O$_2$ first, then in NH$_3$ In one embodiment, the stabilizing agent is a protein or a peptide. Contact of proteins and peptides with the surfaces of silicon-containing material is a common occurrence in a wide variety of contexts, ranging from drug delivery systems to sensors to prosthetics. It has now been found that association between the surface of silicon-containing nanoparticles and proteins or peptides can result in a regular and controlled pattern of OSA production from the degradation product of silicon-based materials. According to the analysis of the particle size distribution in our data, highly uniform particles can be obtained using a peptide or a lipid as a stabilizer. The peptide/protein stabilising agents may be selected in dependence on the type of the formulation and the desire release characteristic of the bioactive compound. In protic formulations, a successful binding peptide/protein has been found to be those which rich in amino (NH) functionality. In aprotic formulations lipid, proteins/peptides (and also lipids) rich in carboxylic or other nucleophilic group functionality (COO—) have been found to be particularly successful. For slow controlled released of OSA it has been found that peptides comprising 10 amino acid residues or fewer are the most effective. For slow release of OSA, the tertiary structure of the peptides has not been found to be significant. In one embodiment, the stabilising agent is a peptide comprising 10 or fewer, for example 8 or fewer, especially 5 or fewer amino acid residues. Advantageously, the peptide has 3 or fewer, for example 2 or 1, amino acid residues. Shorter peptides including a few or even a single amino acid residue with high density of functional group have found to be particularly successful for slow release of OSA. On the other hand for fast release of OSA, the use of larger peptide molecules comprising more than 10 amino acid residues as stabilising agents have been found to be most effective. In one embodiment, the stabilising agent is a peptide comprising more than 10 more amino acid residues, for example 15 or more amino acid residues, especially at least 20 amino acid residues. It has also been found that peptides having a tertiary structure are advantageous for stabilising the fast release of OSA with 3D structure protein such as alkaline phosphatase being particular suitable. Polypeptides and proteins having a net negative charge and/or an excess of carboxyl groups over amine groups, such as albumin, collagen and derivatives thereof, have been found to be particularly suitable stabilizing agents.

Advantageously, the stabilising agent has a weight average molecular weight of 1000 or less, typically 800 or less, especially 500 or less.

In one embodiment, the stabilizing agent is a lipid, for example a lipid having a number average molecular weight in the range of from 500 to 1000. Particularly suitable lipids include phospholipids that comprise a polar head group and one or more hydrophobic chains, especially glycerophospholipids. Particularly suitable phospholipids are those in which the polar head group is linked to quaternary ammonium moieties, such as phosphatidylcholine (PC). The type of lipid may be selected in dependence of the nature of the formulation with neutral or negatively charges lipid being preferred for aprotic formulation while positive charge and small CH$_3$ chain lipids being preferred for protic formulations. Lipids having a hydrophobic chain with a negative head group comprising a carboxyl group are particularly suitable. Preferably the side chain is an aliphatic side chain with 15 or more carbon atoms or an ether side chain with 6 or more repeating ether units, such as a polyethylene glycol or polypropylene glycol chain.

In one embodiment, the stabilizing agent is an electrostatically absorbed species that binds to the surface of the silicon by van der Waal's forces. Preferably, the stabilizing agent has a contact angle less than 45, more preferably less than 20 and ideally less than 10 measured by optical tensiometry, wherein the contact angle of a drop of the stabilising agent on surface of silicon wafer is observed and measured. The lower the contact angle the greater the interaction between the surface and the stabilising agent. Chemical features that result in a good van der Waal's attraction include hydrogen saturated molecules, such as saturated lipids.

In one embodiment, the stabilising agent is or includes a compound that stabilizes OSA in aqueous solutions. A variety of compounds have been found which can serve to stabilise silicic acid in the ortho-form when they are delivered attached to the nanoparticle surface. These include, for example, compounds containing a nitrogen atom with a free electron pair which can form a complex with the silanol groups of the orthosilicic acid and/or silanol groups on the surface of the silicon nanoparticles.

In one embodiment, the stabilising agent is a polar organic compound comprising a high density of polar groups, such as hydroxyl groups or amino groups (e.g. sugars), or compounds with moieties being a formal negative or positive charge, such as salts and zwitterionic species. Suitable stabilising agents include quaternary ammonium compounds, for instance ammonium salts and zwitterionic compounds comprising quaternary ammonium groups such as betaines. Such compounds can be used to allow the formation of acid-stable orthosilicic acid solutions and these can also be attached to the nanoparticle surface to achieve this effect.

Particularly preferred stabilizing agents include organic compounds, including zwitterionic organic compounds, and organic salts having an amino or quaternary ammonium group and a group bearing either an —OH functionality (such as a hydroxyl group, a carboxylic group, a sulfonic acid group or a phosphonic acid group), a deprotonated derivative thereof (for example, a hydroxide), or a ester thereof (such as an acetyl group). Examples of such compounds are amino acids that include an amino group and a carboxylic acid group. In one embodiment, the amino or quaternary ammonium group is linked to the group bearing an —OH, —O⁻, or ester functionality via an $C_{1-6}$alkylene group. In one embodiment, the stabilising agent is a compound or salt of the formula I:

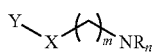
(I)

wherein each R is independently $C_{1-5}$ alkyl or H; n is 2 or 3; m is from 1 to 6 for protic formulations and greater than 6 for aprotic formulations, for example from 7 to 20; X is selected from —CH$_2$—, —C(O)—, —O—P(O)(OR)—, —S(O)$_2$—; and either Y is —OH, —O⁻ or —OC(O)R, where is an aliphatic group, especially a $C_{1-10}$alkyl, $C_{1-10}$alkenyl or $C_{1-10}$cycloalkyl group, preferably a $C_{1-4}$alkyl group. Examples of compound of the formula I that have been found to be effective stabilizing agents include choline and choline derivatives such as acetylcholine, ethanolamine, glycine and glycine derivatives such as N,N,N-trimethylglycine, and taurine, aromatic oil, saturated and unsaturated oil such as Olive oil.

In one embodiment, the stabilising agent comprises a quaternary ammonium moiety. Particularly suitable quaternary ammonium compounds include tetra-alkyl ammonium salts and tetra-alkyl ammonium betaines, wherein each alkyl group contains for instance 1-5 carbon atoms, in particular methyl and ethyl groups. Trialkylhydroxyalkyl quaternary ammonium compounds, wherein the hydroxyalkyl group is preferably hydroxymethyl or hydroxyethyl, for example, choline salts, and derivatives of trialkylhydroxyalkyl quaternary ammonium compounds, such as acetylcholine salts are also effective.

In one embodiment the stabilising agent is a monomeric sugar or dimeric sugar or sugar-like compound such as inositol. In a further embodiment the stabilising agent is a monomeric sugar or sugar-like compound. Suitable monomeric sugars include mannitol and sorbitol.

The stabilising agents may be an osmolytes, such as betaine, inositol, ethanolamine, glycine, taurine and monomeric sugars such as mannitol and sorbitol In one embodiment, the stabilizing agent is an amino acid. The amino acid may be naturally occurring or non-naturally occurring. Suitable amino acids include aspartic acid, glycine, lysine, proline and serine, preferably lysine, proline and serine, especially proline and serine. Amino acids having a net charge, especially a negative charge, having an acidic side chain and/or having more carboxyl than amide groups, such as aspartic acid and glutamic acid, have been found to be particularly suitable. Small amino acids such as amino acids having a molecular mass of 120 or less, especially a molecular mass of 100 or less such as alanine or glycine, especially glycine, have been found to be suitable stabilising agents. Amino acids with hydrophobic side chains such as alanine, isoleucine, leucine, methionine phenylalanine, tryptophan, tyrosine and valine, especially tyrosine, have been found to be suitable stabilizing agents.

In one embodiment, the stabilizing agent is selected from a compound containing a nitrogen atom with a free electron pair which can form a complex with the silanol groups of the orthosilicic acid, a trialkylhydroxyalkyl compound, an osmolyte, a monomeric sugar, a choline derivative and an amino acid.

In one embodiment, the stabilizing agent is a molecule, especially a vitamin or enzyme, having a double conjugate binding and anionic head group such as retinol, retinoic acid, vitamin A or alpha-tocopherol and vitamin D.

A variety of other compounds are known to stabilize solutions of OSA, including the polypeptide stabilizers described in AU 774668 and the quaternary ammonium and amino acid compounds disclosed in U.S. Pat. No. 5,922,360.

In one embodiment, the stabilizing agent is itself a biologically active agent. For example, vitamin A, an agent known to have efficacy in the treatment of acne, has been shown to function as a stabilizing agent. In an alternative embodiment, the composition of the invention may comprise a first compound which functions as a Stabilizing agent and a second compound which is a therapeutically active agent which may or may not also function as a stabilizing agent. Vitamin A, and its in-vivo precursor carotene, have been found to be suitable stabilizing agents. Addition of drugs into the formulation will have a further influence too. According to Brinker, Sol-gel Science & Technology (1990), chapter 3, section 2, the addition of a nucleophile which forms a salt with OSA, for instance sodium to form sodium salt of silicic acid, results in dissociation at lower pH and thus polymerisation at lower pH. Hence polymerisation occurs more slower at ambient pH. For example, OSA has a pKa 8.9 and the introduction of sodium produces Na⁺(OSA)⁻ salt with a pKa about 6 thereby stabilising OSA at lower pH. Stabilising agents such as Vitamin A or amino acids or lipids change the balance of dissociation at biological pH. The addition of a nucleophile produces an OSA conjugate and those conjugates have a lower pKa.

Advantageously, the stabilizing agent is not a polymer. Long chain polymers, for example polymers including 20 or more repeat units have been found to promote silicic acid polymerisation. In particular, polyamides (such as long chain polyallylamine, polylysine and polyarginine), polysaccharides and polyethylene oxides have been found to promote silicic acid polymerisation and so are not suitable for use as stabilizing agents. In one embodiment, the stabilizing agent is not a polymer of 7 or more, for example 10 or more repeating monomer units.

In one embodiment, the stabilising agent is selected from:
1) an amino acid having (a) a net charge, for example a net negative charge, (b) more carboxyl than amino groups, (c) a small structure with a molecular mass of less than 120, and/or (d) a hydrophobic side chain;
2) a polypeptides or proteins having (a) a net charge, (b) a greater number of carboxyl groups than amino groups and/or a 3D structure protein;
3) a phospholipids having a hydrophobic chain and a negatively charged head group;
and/or
4) a vitamin or enzyme having a double conjugate binding and anionic head group.

In some embodiments, the particles may be modified to promote interactions with the stabilizing agent and/or the bioactive compound(s). Furthermore the interaction of carrier system and active compounds may involve linkage and anchor on the surface of silicon. The adsorption of the active compounds on the modified silicon particles prevents the formation of agglomerates.

Delivery of Biologically Active Agents

The composition of the first aspect of the invention is advantageously a drug delivery system that comprises at least one bioactive ingredient, such as an active pharmaceutical agent or other beneficial compound, in addition to the silicon-containing material. In one aspect, the invention provides the use of the nanoparticles of the invention as a delivery system for a bioactive agent. A beneficial compound is any organic compound used in therapy or diagnosis which has an overall beneficial effect on the patient to which it is administered.

In one embodiment, the stabilizing agent is a bioactive ingredient. In a further embodiment, the composition of the first aspect of the invention comprises a biologically active ingredient, or a further biologically active ingredient, in addition to the stabilizing agent. According to one aspect, the composition of the present invention is a composite nanomaterial comprising a nanoparticulate silicon semiconductor impregnated with at least one bioactive ingredient. Optionally, the bioactive ingredient is present in an amount of at least 1% by weight, for example, at least 5 wt % and typically 15 wt % or more based on the total weight of the composition. The bioactive compound may be present in significantly greater levels than those described above, especially in embodiments in which the bioactive agent functions as a stabilizing agent (i.e. where the stabilising agent is itself a bioactive agent). In such embodiments, the bioactive agent is advantageously present at a level of at least 50% by weight, for example at least 65% by weight based on the total weight of the composition.

The composition can be used to deliver to the body a wide variety of materials including large molecules, such as proteins and enzymes, unstable compounds such as peptides and low-solubility materials such as some vitamins. Particularly advantageously, compositions according to the present invention may be used to deliver high doses of poorly water soluble or hydrophobic organic compounds. The dissolution rate of the drug into aqueous bodily fluids following administration impacts on the bioavailability of the drug and so compounds which have low aqueous solubility tend to be poorly bioavailable following administration, leading to difficulties in rapidly attaining therapeutically effective drug levels. This represents a significant problem in the development of pharmaceutical compositions containing such active ingredients. By providing the beneficial organic substance in the compositions of the present, the surface area of the organic substance available to contact the aqueous media at the site of administration or site of absorption is maximized, thereby enhancing its dissolution rate and hence the bioavailability.

In one embodiment, the bioactive ingredient comprises a retinoid, such as vitamin A. Unlike the water soluble peptide hormones and growth factors, which bind to cell surface receptors, the retinoids are fat soluble hormones that can pass through the lipid bilayer of the cell membrane, after which they are free to interact with intracellular proteins. This hormone-receptor complex is able to initiate the GIT cellular response. There are several proteins found which bind in vivo retinol and retinoic acid. Extracellular retinol is transported from retinoid stores in the liver to target tissues by binding the extracellular retinol binding protein (RBP). Retinoids such as vitamin A pose particular formulation difficulties as they are not only poorly soluble and chemically unstable but are also known to exhibit toxic effects which damage the development of cells in foetuses, leading to the developments of conditions like spina bifida, hydrocephalus and urinary tract malformations. Pregnant women and those trying to conceive are therefore advised not to take prescription acne drugs related to retinol (a compound of vitamin A), including topical tretinoin (Retin-A) due to the risk of birth defects associated with too high an intake of vitamin A.

By formulating retinoids such as vitamin A in a composition according to the present invention, a safer product with increased solubility and stability may be obtained. The amount of active ingredient needed to produce a therapeutic effect is decreased compared to conventional retinoid formulations and sustained drug release is possible due to the incorporation of the drug within the solid matrix of the silicon nanoparticles. This affords the possibility of supplying the active ingredient over a prolonged period of time, thereby helping to reduce systemic absorption following topical administration and rendering the formulation safer for use by pregnant women and those trying to conceive.

Formulations for Topical Administration

The compositions of the invention have been found to be particularly suited for topical administration. According to one embodiment of the a first aspect of the present invention, there is provided a topical composition comprising nanoparticles of a hydrolysable silicon-containing material wherein the surface of the silicon-containing material is modified by association with, for example attachment of, a compound which stabilises the silicic acid produced upon hydrolysis of the silicon in its ortho-form.

In one aspect, the invention provides the use of such nanoparticles as a topical delivery system for a bioactive agent. The invention further provides compositions, for example topical compositions, comprising such nanoparticles and a bioactive agent, methods for preparing such compositions, and their use in a method of cosmetic treatment of the human or animal body or in a method of treatment of the human or animal body by therapy or diagnosis. Use of nanoparticles as a topical delivery system enhances the penetration of the bioactive compound(s). As the particles are nanosized, they are able to penetrate into the deep layers of the skin where their gradual dissolution can allow controlled release of bioactive compounds through the tailoring of stabilising agents.

In another embodiment, the invention provides a topical composition, wherein the compound which stabilises silicic acid in its ortho form is selected from a compound containing a nitrogen atom with a free electron pair which can form a complex with the silanol groups of the orthosilicic acid, a trialkylhydroxyalkyl compound, an osmolyte, a monomeric sugar, a choline derivative and an amino acid.

Silicon-containing nanoparticles with a high level of bioactive ingredient may therefore suitably be formulated as cosmeceutical products for controlled release. In particular, these nanoparticles may be applied into the target site using a fine powder or lotion.

The invention advantageously provides hydrolysable silicon-containing nanoparticles which may be used for the topical delivery of active ingredients. Compositions incorporating these nanoparticles provide a means of delivering such bioactive substances while avoiding the need to incorporate further ingredients for enhancing skin permeability and cell stimulation. Such compositions are therefore safe and cost effective. By means of the invention, compositions are provided which enable both the silicon-containing nanoparticles and any bioactive ingredient(s) associated therewith to penetrate to the deeper layers of the skin and ensure uptake by the cell membrane. As the hydrolysable silicon-containing nanoparticles are themselves biodegradable, they have the advantage that further processing, such as porousification is not essential. Since degradation is gradual, the bioactive degradation products, and any other active ingredients associated with the particles, can be released at a controlled rate over a sustained period of time. Furthermore, OSA can be absorbed by skin cells with beneficial results. For skin diseases and skin disorder treatment use of nanoparticles beads can be used both as an exfoliate and for delivery of beneficial compounds, such as antibiotics and anti-inflammatory agents, to the skin.

Upon application on or within the skin, the hydrolysable silicon material containing nanoparticles advantageously biodegrade at a gradual rate thus inducing the controlled release of both the active compound(s) and the bioactive silicic acid. The mechanism of the release is dissolution and diffusion. While the nanoparticles silicon-containing material dissolves, the active compound(s) dissociates from the nanoparticles and is released into the skin. At the same time, the degraded silica, i.e. monosilicic acid, is absorbed by the skin cells.

The bioactive delivery system according to the invention may conveniently be formulated into any conventional topical composition and administered to the subject to be treated in a manner consistent with the dosage formulation and in an amount which is prophylactically and/or cosmetically or therapeutically effective. Typical topical compositions take the form of lotions and creams. These offer a wide range of potential applications, including the delivery of compound(s) for skin care, cosmetic applications, such as the release of anti-aging or age reversal compounds into the skin, the treatment of skin wounds and the treatment of skin conditions, such as acne or psoriasis.

Surface Modifications to the Silicon-Containing Materials

In one embodiment the silanol groups are linked to the stabilizing agent via a surface modifying group. Unmodified nanoparticles comprising hydrolysable silicon have only silanol hydroxide groups on the surface and are not suitable for the preparation of inorganic-organic composite materials. Functionalisation of silica particles leads to the presence of active groups on the particle surface allowing binding to other molecules. For example the surface of the silicon-containing material can be modified to include chloride, —$NH_2$ (amine), —SH (thiol), —POO and —COOH (carboxylic acid) functional groups. In particular, it has been found that the modification of silica with carboxyl groups increased the ability of the silicon containing material to bind to stabilizing molecules enabling the controlled release of OSA.

Methods for cross-linking organic substances to surfaces are well known in the art and include use of reagents such as glutaraldehyde and carbodiimides such as 1-ethyl-3-(3-5 dimethylaminopropyl)carbodiimide (EDAC). These methods can suitably be used to couple the orthosilic acid-stabilising agent to the silicon-containing nanoparticle surface.

It will be appreciated that the choice of reagent will depend on what functional groups are available for linkage in the substance chosen to be attached, whether these groups can react without adversely affecting the functional properties of the substance and the sensitivity of the beneficial substance to the conditions required for the cross-linking reaction.

In order to enable covalent linking to the silicon surface, the surface of the porous silicon will generally firstly need to be derivatised to form either Si—O or Si—C bonds to groups which in turn may themselves be linked to the desired chemical species. Suitable surface modification methods are well own in the art and include thermal, electrochemical or chemical oxidation methods.

Silicon-Containing Materials

As used herein, the term "a hydrolysable silicon-containing material" is any silicon-containing material which, upon administration to a human or animal subject, may be converted to silicic acid in a timely manner. Typically, 1 mg of nanoparticles of the hydrolysable silicon-containing material hydrolyse in 100 mL of physiological buffer, for example PBS, within one hour at 37° C. Suitable silicon-containing materials typically include at least 50 wt % silicon, for example at least 70 wt % silicon. The silicon-containing materials may be substantially pure silicon, for example, materials comprising at least 90 wt % silicon, preferably at least 95 wt % silicon, especially at least 99 wt % silicon. The hydrolysable silicon-containing material is typically a semiconductor material such as amorphous silicon. Semiconductor grade silicon typically comprises very high levels of silicon, for example at least 99.99 wt %. Substantially pure silicon materials may, optionally, include trace amounts of other elements, such as boron, arsenic, phosphorus and/or gallium, for example as semiconductor doping agents. The substantially pure silicon material may be a p-type doped silicon wafer, for example containing trace amounts of boron or another group III element, or n-type silicon wafers, for example containing trace amounts of phosphorous or another group VI element. The surface of the silicon material typically includes silanol (Si—OH) groups. Suitable hydrolysable silicon-containing materials for use according to the invention include but not limited to nanosilicon (single or poly crystal), of semi conductive grade and nanosilica.

Suitably, the silicon content of the composition of the invention is within the range of 0.01-50 wt. %, preferably within the range of 0.01-10 wt %, more preferably within the range of 0.1-10 wt %, and most preferably within the range of 0.1-5 wt %. In one embodiment, the silicon content of the composition is in the range of from 1 to 30 wt %, for example from 2 to 20 wt %, preferably from 3 to 15 wt % based on the total weight of the composition. The total silicon content is dependant on the biologically active molecule being delivered and the application. Accordingly, the composition may be used in a dosing regime which is suitable for most pharmaceutical, skin care and cosmetic utilities.

Nanoparticles

The term "nanoparticle" is typically used to describe a particle having at least one dimension in the nanometer range, i.e. of 300 nm or less. The nanoparticles for use according to the invention typically have an average particle diameter of less than 300 nm, preferably less than 200 nm and especially less than 100 nm. In one embodiment, the nanoparticles have an average particle diameter in the range of from 10 to 100 nm, preferably from 20 to 80 nm and especially from 20 to 50 nm. The average particle diameter is the average maximum particle dimension, it being understood that the particulars are not necessarily spherical. The particle size may conveniently be measured using conventional techniques such as microscopy techniques for example scanning electron microscopy.

In one embodiment, the nanoparticles for use according to the invention have a spherical or substantially spherical shape. The shape may conveniently be assessed by conventional light or electron microscopy techniques.

It has been found that by decreasing the size of silicon particles from the micron to the nanometer range, a biodegradable delivery system can be provided which does not require the use of porous material. Microparticles typically have an average diameter in the range of from 1 to 1000 μm, for example from 0.7 to 700 μm. Silicon nanoparticles have been found to be biodegradable and suitable for loading with high levels of bioactive ingredient without the need for the silicon to be porous. This affords the possibility that high doses of beneficial organic substance can be delivered over a period of time and in a controlled manner. This also eliminates the need to create porous material using hydrofluoric acid, which is a highly hazardous substance, thereby enhancing the safety of the formulation and the method by which the formulation is produced while still able to provide a biodegradable carrier system.

Preparation of Silicon-Containing Nanoparticles

The silicon-containing nanoparticles according to the invention may conveniently be prepared by techniques conventional in the art, for example by milling processes or by other known techniques for particle size reduction. The silicon-containing nanoparticles made from sodium silicate particle, colloidal silica or silicon wafer materials. Macro or micro scale particles are ground in a ball mill, a planetary ball mill, plasma or laser ablation methods or other size reducing mechanism. The resulting particles are air classified to recover nanoparticles. We also use plasma methods and laser ablation for nanoparticles production.

Following size reduction of particles the incorporation of stabilizing agent and, optionally, (further) biologically active molecules will proceed. By modifying the surface chemistry of nanoparticles silicon-containing material the compounds can be coupled by ionic, covalent or H bonds to an agent to be delivered or to a ligand which forms a complex with the agent to be delivered. In one embodiment, the nanoparticles may be hollow. Hollow nanoparticles may be prepared by methods conventional in the art. For example, hollow silica nanoparticles may be prepare by synthesizing a layer of silica on tiny spheres of colloidal gold and then dissolving the gold interior, leaving a hollow silica shell. (K. R. Brown, D. G. Walter and M. J. Natan. (2000) Seeding of Colloidal Au Nanoparticle Solutions. 2. Improved Control of Particle Size And Shape. *Chem. Mater.* 12: 306-13). The (si) deposition may conveniently be achieved by hydrolysis of a silicate, such as a monomeric silicate (for example silicon halogenide, methyl orthosilicate, sodium or magnesium orthosilicates), or a hydrated silicate, such as crystalline sodium silicate.

Where the hydrolysable silicon-containing material is present in the form of hollow nanoparticles, the bioactive ingredient(s) may suitably be contained within the hollow nanoparticles. The interior of the hollow nanoparticles may be loaded with bioactive ingredient by conventional methods known in the art such a incubation and/or lyophilisation methods. Alternatively, one or more bioactive ingredients for delivery to the skin may be adsorbed or otherwise fixed at the external surface of the nanoparticles according to the invention.

Impregnation of the Bioactive Ingredient

Adsorption of the bioactive ingredient to the external surface of the nanoparticles may suitably be achieved using conventional techniques such as coating of surface and/or modifying the surface of particles such as creating a surface charge. The nanoparticles according to the invention may optionally incorporate targeting molecules on their external surface for providing targeted delivery of the active compound to the skin or other organs or tissues. Suitable targeting molecules include peptides, proteins or antibodies and these may be incorporated by any method conventional in the art of targeted delivery such as covalent attachment. Bioactive ingredients which may be delivered to the skin by means of the nanoparticle delivery system according to the present invention include any agents which when administered elicit a desired cosmetic, therapeutic or diagnostic effect. Suitable agents for skin care which may be delivered using the present delivery system include enzymes, vitamins, proteins, peptides such as Q10 enzyme, vitamins A or E, DNA and oligonucleotides. Suitable therapeutic areas include but are not limited to skin cancer therapy, Antiemetics, Muscle relaxants, Neuropathy drugs, NSAIDs, analgesics, hormones, antibiotics and topical microbicide for the prevention of the vaginal transmission of STIs. Diagnostic agents which may be administered alone or coupled to one or more therapeutic agents as described above. The agents can be radiolabelled, fluorescently labelled, enzymatically labelled and/or include dyes or magnetic compounds and other materials that can be detected using x-rays, ultrasound, magnetic resonance imaging ("MRI"), positron emission tomography (PET), computer assisted tomograph ("CAT"), single photon emission computerized tomography, fluoroscopy or other commonly used diagnostic technology.

Surface Chemistry

The surface chemistry of the particles can control dissolution rate through manipulation of the active "surface area". The idea of an active surface area is important when considering loaded silicon surfaces, i.e. particles with a foreign agent on their surface. This foreign substance will most likely be the drug and/or stabilising agent in the formulations of the invention but the active surface prior to loading is just as important.

Silicon is a reactive element as such its preparation into a powder regardless of size is likely to result in some form of functionalisation of the surface. An example is that of silicon wafer. As prepared the wafer is oxygen free however is rapidly oxidised in air resulting in a thin oxide layer on the wafer. Thermal treatment and washing tend to increase this layer thickness. Thus it can be expected that ball milling or other methods of production for nano silicon are likely to leave an oxidised surface or one that will oxidise on exposure to the atmosphere.

These coatings limit the amount of the silicon surface, water has access to and hence the dissolution rate. Thus dissolution of particles will have two kinetic parameters dissolution of the particle "coating" and dissolution of the pure silicon core. The kinetics of drug coatings can be measured directly by measurement of drug elution as a function of time. Whist measurement of a surface oxygen layer is not possible by this method as the oxidised surface will dissolve to silicic acid and be indistinguishable from the silicic acid produced from the core of the particle. However the slope of dissolution should show a lag phase as the oxide layer is dissolved prior to the dissolution of the silicon core.

The amount of oxygen (and its type hydroxyl peroxo etc) on the particles can be determined as a % of the total silicon by XPS, this can be useful to estimate oxide thickness.

Particle Environment

As discussed above the chemical environment strongly determines the rate and final product in the dissolution of silicon.

The compositions of the invention bias the equilibrium between OSA and PolySA such that it is kept on the monomeric side to allow complete biocompatibility. The above description represents a simple solution of silicic acid with small concentrations of acid or base. When there are significant concentrations of other species present equilibrium side reactions with these ions occur to form alternate by-products than silica $SiO_2$. This in turn shifts the equilibrium away from $SiO_2$ allowing a longer life time for silicic acid and a greater chance of its excretion. Functionalisation of silicon with organic molecule has been well studied for the sol-gel process. The kinetic data for the conversion of functionalised silicates shows dissolution can be accelerated or decelerated depending on the electronegativity of the functional group, and the by-products pKa see Brinker chapter 3, section 2.

EXPERIMENTAL

The invention may be further illustrated by the following non-limiting examples.

The data provided below shows by varying the physical and chemical parameters, e.g. particle size or specific surface area of a starting material, silicic acid of a desired form (Ortho), and amount, can be obtained in a controlled manner through linkage in a surface and within pores of silicon. The further production of OSA is depends on the choice of stabiliser/active compound and the dosage of these in the formulation.

Sample Preparation and Treatment.

1. Silicon

Single side polished p-type or N-type silicon wafers were purchased from Si-Mat, Germany. All cleaning and etching reagents were clean room grade. Etching silicon were prepared by anodically etching of p-type Si in a 1:1 (v/v) pure ethanol and 10% aqueous HF acid for 2-10 min at an anodic current density of 80 mA/cm$^2$. After etching, the samples were rinsed with pure ethanol and dried under a stream of dry high-purity nitrogen prior to use.

Etched Silicon wafer, P+ or N− crushed using a milling ball and/or pestle & mortar. The fine powder sieved using retsch branded sieve gauge 38 um and shaker as200. Uniform and selected sizes (20-100 um) is achieved by the aperture size of the sieve. The particles sizes were measured by the quantachrome system and PCS from Malvern instrument. Samples keep in the close container until further use. NanoSilicon powder also obtained from Sigma and Hefel Kaier, China. The particle size measured by PCS and the size of the particles recorded (size was range between 20-100 nm) before subjected to the loading and etching. Silicon wafer was crushed using a milling ball, or using mortal & Pestle. The fine powder was sieved using a retsch branded sieve gauge 38 um and shaker as200 and uniform nanoparticles with desired size collected. A solution of a stabilizing compound was prepared. [Unless otherwise said the stabilisers solution prepared as follow: 5 mg of stabiliser (AA or peptide) was dissolved in 25 mL of distilled water and 1 mL of HCl [0.01M] or 1 ml DMSO was added to dissolve completely in the solution. The DMSO also used to enhance stability of AA/peptide in the formulation. Then the volume is completed to 50 mL using distilled water. The final concentration was 100 µg/mL. In case the stabiliser is vitamins or lipids 5 mg of agent was weighed and was dissolved in 5 ml of ethanol (99%). The final concentration was 100 µg/mL.

Activated Silicon Stock Solution—300 mg of nano-silicon was added to a solution of 1500 ml 10% NaOH and 300 ml of glycerol with gentle stirring using a magnetic bar. After 30 minutes the solution was neutralized using concentrated HCl (4N) until a pH of 5.5-7.0 was achieved. The volume was made up to 2000 ml with distilled water.

OSA production measured by the Molybdenum blue assay. The percentage amount of OSA release from the formulation was measured using UV vis spectra at wave length $\lambda_{max}$ (700 nm). The process was repeated 3 times and the average data was taken.

Molybdenum Reagent preparation using literature information. In brief reagents prepared as:

0.2M of HCl

1% w/v of Ethylene Di-amine Tetra Acetic acid (EDTA) in DW

5% w/v of Ammonium Molybdenum [(NH$_4$)$_6$Mo$_7$O$_{24}$.4H$_2$O] in DW.

17% w/v of sodium sulphite using DW.

Figure 9:
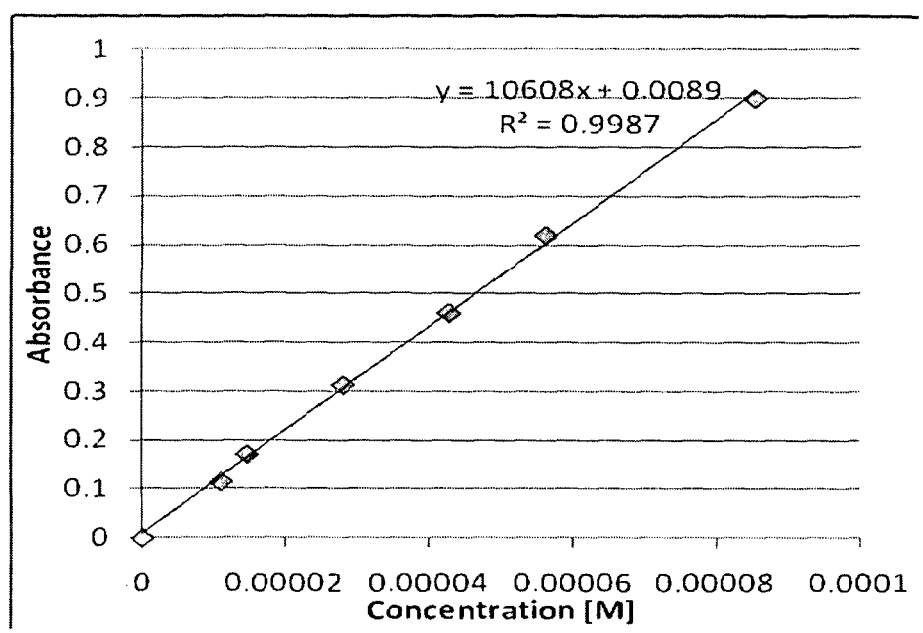
FIG. 9 provides the calibration curve of OrthoSilicic acid at $\lambda_{max}$ 700 nm.

I—Calibration Curve for OSA:

To investigate the absorbance factor of Orthosilicic acid, a various known concentration of orthosilicic acid (Sigma product) made from standard solution (1 mg/ml). Each concentration subjected to Molybdenum assay and read by UV at 700 nm. The calibration curve for OSA is provided in FIG. 9.

The absorbance factor ($\epsilon$) of Orthosilicic acid was obtained from the relation slope of the straight line curve between silicic acid concentrations via absorbance. The ($\epsilon$) value was equal to 10608 cm·L·mol$^{-1}$ with $R^2$=0.998, 2. Loading Methods Method A A loading solution of hydrophobic stabilizing compounds was prepared by dissolving 200 mg of the stabilizing compounds into 3 mL of ethanol.

1. The unloaded silicon powder was weighed.
2. The stabilizing compounds were slowly added to the particles portionwise and the liquid was allowed to penetrate to the pores in case of etched particles or interact with surface of non-etched silicon for several minutes. Using a gentle heat (>70° C.), allowed the liquid to evaporate. This step was carried out several times until all the stabilizing compound solution had been introduced to the powder.
3. Excess loading material was removed with an ethanol wash and the surface of the silicon particles was allowed to completely dry before proceeding.
4. The silicon/stabilizing compound mixture was reweighed, the weight difference being due to the loading of the stabilizing compound.
5. The dry samples were kept in the fridge until further use.

Method B

A loading solution of hydrophilic, biological and heat sensitive compounds was prepared including peptide, protein, and amino acids by dissolving 5 mg of the stabilizing compounds in 25 ml of distilled water followed by the addition of 1 ml of HCl [0.01M]. For proteins the addition of HCl was not required as they dissolved fully in distilled water.

1. The unloaded silicon powder or wafer was weighed.
2. The stabilizing compounds were slowly added to the particles portionwise and the liquid was allowed to penetrate to the pores in case of etched particles or interact with surface of non-etched silicon for several minutes. The liquid was evaporated using a Freeze-Dryer or rotary evaporator. Depending on the amount of the active compound and the volume the material was left from 1 h to 24 h in the Freeze-Dryer until the powder was completely dried. This step was carried out several times until all the stabilizing compound solution had been introduced to the powder.
3. The samples were rehydrated with 1-2 ml of saline or distilled water.
4. The samples were left at room temperature for 1 h.
5. Additional distilled water was added to make up the volume to 20-100 mL, depending on the initial amount of silicon:stabilizing compound and the sample was left for another hour at room temperature.
6. The material was transferred to centrifuge tube and the mixture was centrifuged to remove loss binding and non-binding stabilizing compound.
7. The supernatant was collected and the pellet was rehydrated.

8. An analytical or biological tool was used for the reading. UV absorbance for was used for most compounds, such as amino acids, and/or HPLC for specific compound including small molecules
9. The dry samples were kept in the fridge until further use.

The centrifuge step was omitted for some of the amino acid studies. It is not necessary to do centrifuge steps if the product doesn't require to fully wrapping within particles.

The method A and B has been used for both particles and silicon wafer. In the case we had an experiment with wafer we preferred to use F-D or heating method rather than rotary evaporator.

The starting compounds are examined using usually HPLC for their active moiety to verify that their synthesis has been successful considering the structural properties and phase purities using FTIR, Raman and HPLC. The stabilizing agent incorporated matrices are studied to determine if the loading procedure has been efficient i.e. to determine if the stabilizing agent has adsorbed into the surface of nanoparticles. In the case of successful attachment, the structural state of the drug is qualified (crystalline or molecular amorphous) and the amount adsorbed quantified (w/w %). The characterization methods used for this are x-ray powder diffraction (XRPD), nitrogen adsorption (SSA and pore size distribution), pycnometry (density), differential scanning calorimetry (DSC) and thermogravimetry (TG).

Example 1

Effect of Particle Size on the Production of OSA 4 mg P dope Silicon particles prepared using mill balling (for micron size) and plasma (for nano size) methods. Particles size measured prior dissolution study (300 micron and 20 nm) using PCS. In this study samples of micron or nano particles didn't subject to surface modification. The amount of OSA production was investigated in native surface form of silicon.

Example 2

Effect of a Silicon Surface Modification on the Production of OSA 3 mg of silicon powder (micron and nano) was collected from stock solution of activated silicon. (Silicon surface modified as described above.)

Each samples transfer to the dialysis bag and put into a 50 mL PBS. Each bottle was sealed and put in water bath (37° C.). Aliquot of 2 mL collected and OSA production measured using UV by the Molybdenum blue assay.

The non-activated surface samples also weighed (3 mg micron and 3 mg nano) used as a control samples in this study.

Example 3

Effect of a Stabilizing Agent on the Production of OSA 3 mg of silicon powder (micron and nano) was collected from stock solution of activated silicon (Silicon surface modified as described above.)

Each sample contains 3 mg of Silicon formulated with a different active compound (AC) using method A for Vitamin A (Si:AC; 1:2 ratio) and method B for amino acids (Si:AC; 1:2 ratio).

Silicon as such i.e. without link to the stabiliser used as a control. All the samples rehydrated and left at RT for overnight. Samples subjected to centrifuges for 50 min. at 30,000 rpm. Supernatant has been collected and amount of OSA release was measured by reading the supernatant absorbance using UV spectra ($\lambda_{max}$=700 nm). Each pellet re-suspended and left at RT and the process repeated for three consecutive days. Each formulation made in triplicate. In brief 2 mL of HCl, EDTA and Molybdenum solutions were added to 7 clean and dried test tubes and left for 5 minute. 2 mL of formulation added to reagent and the amount of OSA in the solution read by UV spectra.

Table 1 shows the amount of OSA produced:

| Compound | Surface activated | Stabiliser | Starting amount of silicon | Amount of OSA production | | |
|---|---|---|---|---|---|---|
| Silicon | — | — | 2.9 mg/L | 9.6 mg/L 0.48 mg/50 ml | (Theoretical value) | |
| Nanosilicon | — | — | 3 mg/50 ml | 0.28 mg/50 ml | | |
| Nanosilicon | yes | — | 3 mg/50 ml | 0.91 mg/50 ml (1 h) | 0.78 mg/50 ml (24 h) | 0.7 mg/50 ml (48 h) |
| Nanosilicon | Yes | Asp (AA) | 3 mg/50 ml | 1.05 mg/50 ml (1 h) | 1.10 mg/50 ml (24 h) | 1.11 mg/50 ml (48 h) |
| Nanosilicon | Yes | Lipid (PC) | 3 mg/50 ml | 0.99 mg/50 ml (1 h) | 1.07 mg/50 ml (24 h) | 1.10 mg/50 ml (48 h) |
| Nanosilicon | Yes | Vit.A | 3 mg/50 ml | 1.02 mg/50 ml (1 h) | 1.09 mg/50 ml (24 h) | 1.16 mg/50 ml (48 h) |

Each sample was placed in dialysis bag and each bag was left vertically down to the 20 ml PBS (pH at 7.4) bottle. The bottle top sealed and left in 37 C water bath. 2 ml aliquot was sampling out of 20 ml solution for 7 days. % of OSA was determined by measuring the amount of dissolution of Si using UV vis by the mean of Molybdenum blue assay.

FIG. 1 demonstrates that the production of OSA is substantially enhances by the use of silicon nanoparticles compared with micron particles.

Figure 3:
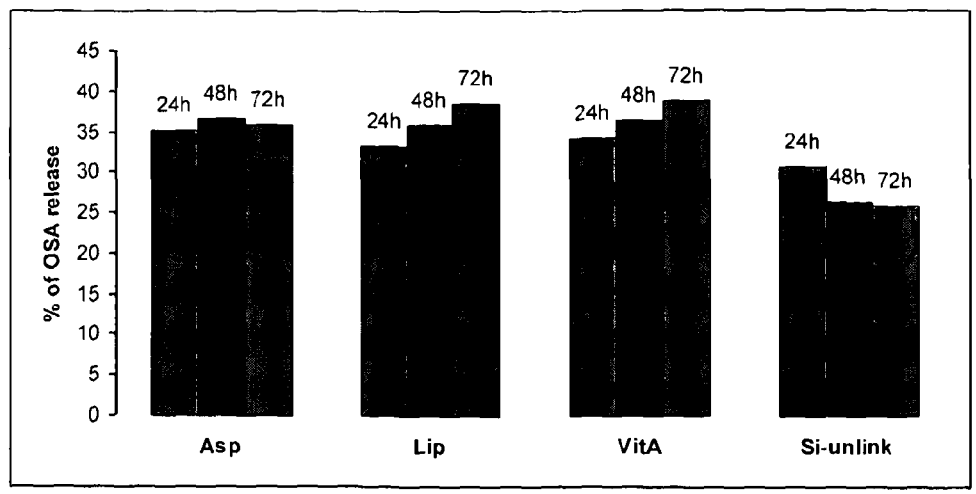
FIG. 3 shows the production of OSA as a percentage of silicic acid species over time with aspartic acid, lipid or Vitamin A stabilising agents.
Figure 4:
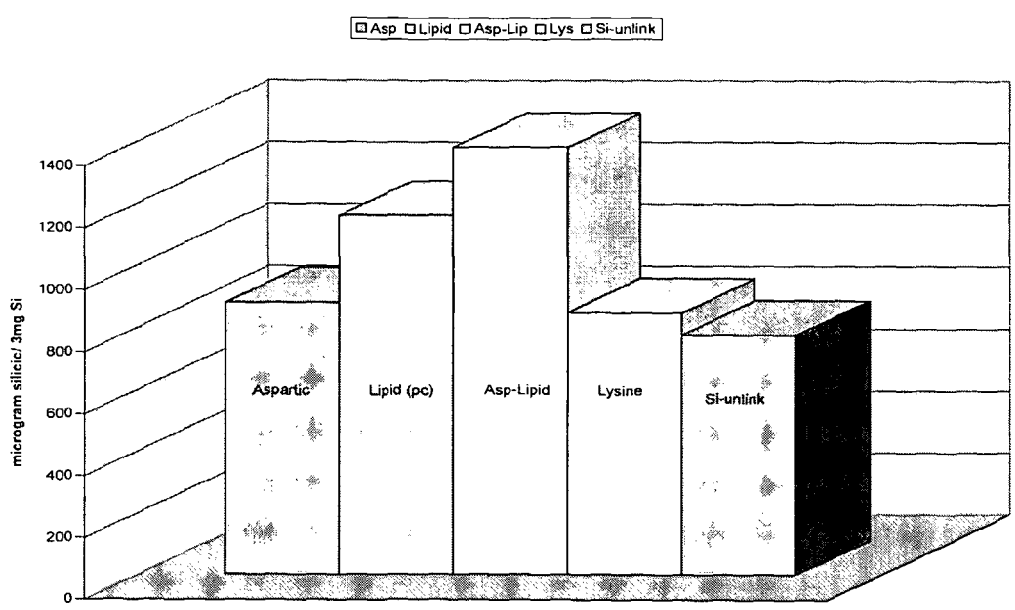
FIG. 4 shows the micrograms of OSA produced per 3 mg silicon when the silicon nanoparticles are complexed to aspartic acid, a lipid, a combination of aspartic acid and a lipid, lysine or no stabilizing agent.

FIG. 3 and FIG. 4 demonstrate that there is a significant increase in production of OSA when silicon was linked with stabiliser such as an amino acid and/or other active ingredient compared to that produced by silicon nanoparticles in the absence of a stabilizing agent. Furthermore, although unlinked nanosilicon initially resulted in high concentrations of OSA (0.91 mg/50 ml after 1 hr) in solution, in the absence of a stabilising agent, the concentration of OSA then diminished. It is believed that the presence of the amino acid slows the degradation allowing silicon dissolve to OSA and stay in that form as the concentration remains below the levels were significant polymerisation occurs. It has been found that the type of amino acid effects the production of OSA. When nanoparticles treated with tyrosine the production of OSA is close to the group of unlinked nanoparticles while aspartic acid demonstrated twice production of OSA compare to the non-linked one. The formulation treated with Vitamin A provided a similar OSA production performance as the one treated with aspartic acid.

Example 4

Effect of Surface Activation

First group—Nanoparticles P doped silicon weighed and transfer into 7 tubes. Each tube contained 3-5 mg surface activated nano-silicon. Selected active compounds transfer into each tube and formulated using method A for vitamin A and lipid (PC) and method B for AA. The ratio between silicon to active compound was kept constant in all tubes (1:2 Si to AC).

The second group was prepared exactly as first group on the amount of silicon and the amount of the active compounds in the formulation. However in this group silicon surface didn't activate. All the samples rehydrated and left at RT for overnight. Samples subjected to centrifuges for 50 min. at 30,000 rpm. Supernatant has been collected and amount of OSA release was measured by reading the supernatant absorbance using UV spectra ($\lambda_{max}$=700 nm). Each formulation made in triplicate. In brief 2 ml of HCl, EDTA and Molybdenum solutions were added to 7 clean and dried test tubes and left for 5 minute. 2 ml of formulation added to reagent and the amount of OSA in the solution read by UV spectra.

The majority of the work has been carried using the Hitachi UV2001 UV spectrometer using a wavelength of 700 nm. HPLC methods have also been used for the analysis of dissolution samples, integrity of active compounds, and amount of incorporation of active ingredient within nanoparticles.

TABLE 2

Molybdenum reagent with silicon solution to determine OSA concentration

| Tube | HCl (ml) | EDTA (ml) | Molybdenum Solution (ml) | Sodium Sulphite ml | Test Solution | Total volume | Dilution Factor |
|---|---|---|---|---|---|---|---|
| Vit A | 2 | 2 | 2 | 2 | 2 | 8 | 0.206 |
| Asp | 2 | 2 | 2 | 2 | 2 | 8 | 0.0625 |
| Lipid | 2 | 2 | 2 | 2 | 2 | 8 | 0.206 |
| VitA + Asp | 2 | 2 | 2 | 2 | 2 | 8 | 0.057 |
| VitA + Lip | 2 | 2 | 2 | 2 | 2 | 8 | 0.173 |
| Asp + Lip | 2 | 2 | 2 | 2 | 2 | 8 | 0.057 |
| Silicon | 2 | 2 | 2 | 2 | 2 | 8 | 0.25 |

After 30 minutes the absorption of the samples was measured using UV-Vis spectra at wavelength of ($\lambda_{max}$) 700 nm. The absorbance measurement was repeated 3 times and the average data was taken. The absorbance was used to calculate the level of OSA present in the tubes as a percentage of the total silicic acid content.

Figure 5:
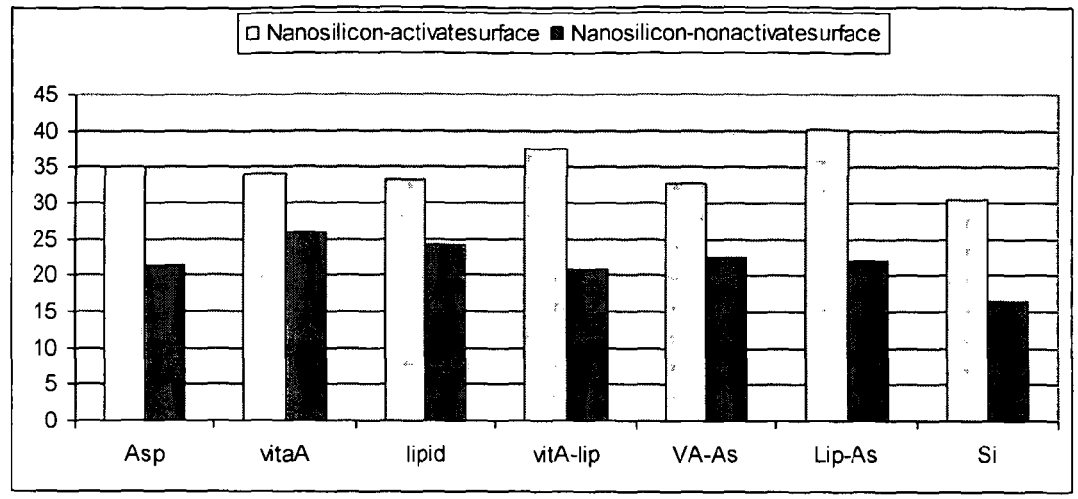
FIG. 5 shows the effect of activating the surface of silicon prior to complexing with various stabilising agents on the production of OSA.

The above procedure was performed using both the stock solution of non-activated silicon and the stock solution of activated silicon. FIG. 5 shows that when silicon is treated with stabiliser without prior activation of the silicon surface, see right hand columns, the production of OSA is less than when the stabiliser is liked to the silicon nanoparticles after surface activation.

Figure 2:
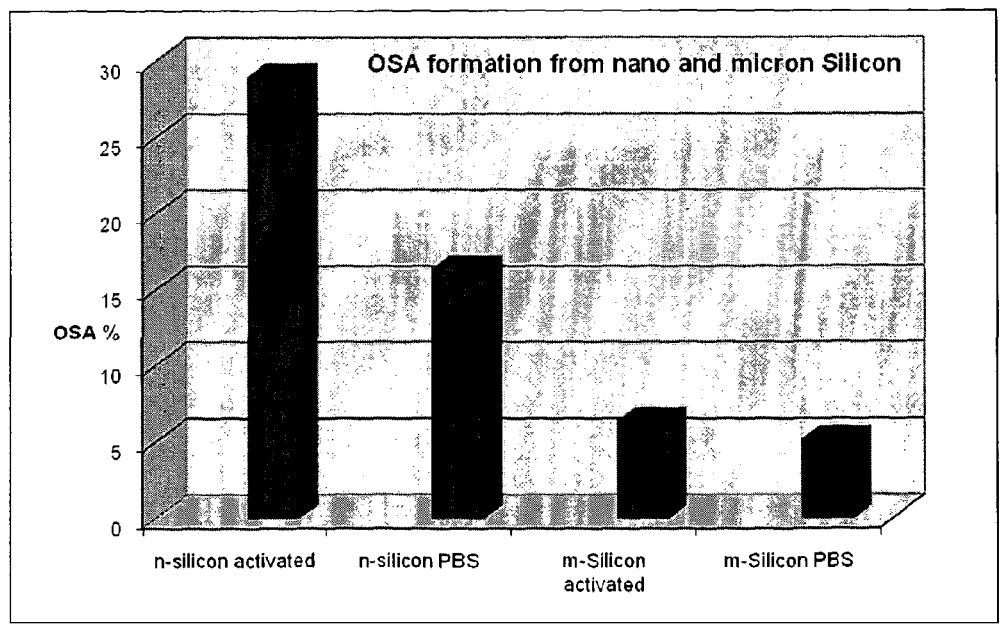
FIG. 2 shows the effect of surface modification Production of OSA.

The effect of surface activation on both nano and micron particle on production of OSA was also investigates. FIG. 2 shows that while with micron the data shows this effect was minimum the production of OSA enhanced significantly when surface of silicon is treated with NaOH and HCl.

Example 5

Polymerisation of OSA from Nanoparticles in the Absence of a Stabiliser 3 mg of nano silicon powder which previously activated using previously described method weighed and transfer to 3 universal tubes. All three samples have gone through the process using for formulation without using any active compound. Samples made to 50 ml volume and left over night at RT. Samples subjected to centrifuges for 50 min. at 30,000 rpm. Supernatant has been collected and amount of OSA release was measured by reading the supernatant absorbance using UV spectra ($\lambda_{max}$=700 nm). Each pellet re-suspended and left at RT and the process repeated for four consecutive days. Each formulation made in triplicate.

In brief 2 ml of HCl, EDTA and Molybdenum solutions were added to 7 clean and dried test tubes and left for 5 minute. 2 ml of formulation added to reagent and the amount of OSA in the solution read by UV spectra.

Figure 6:
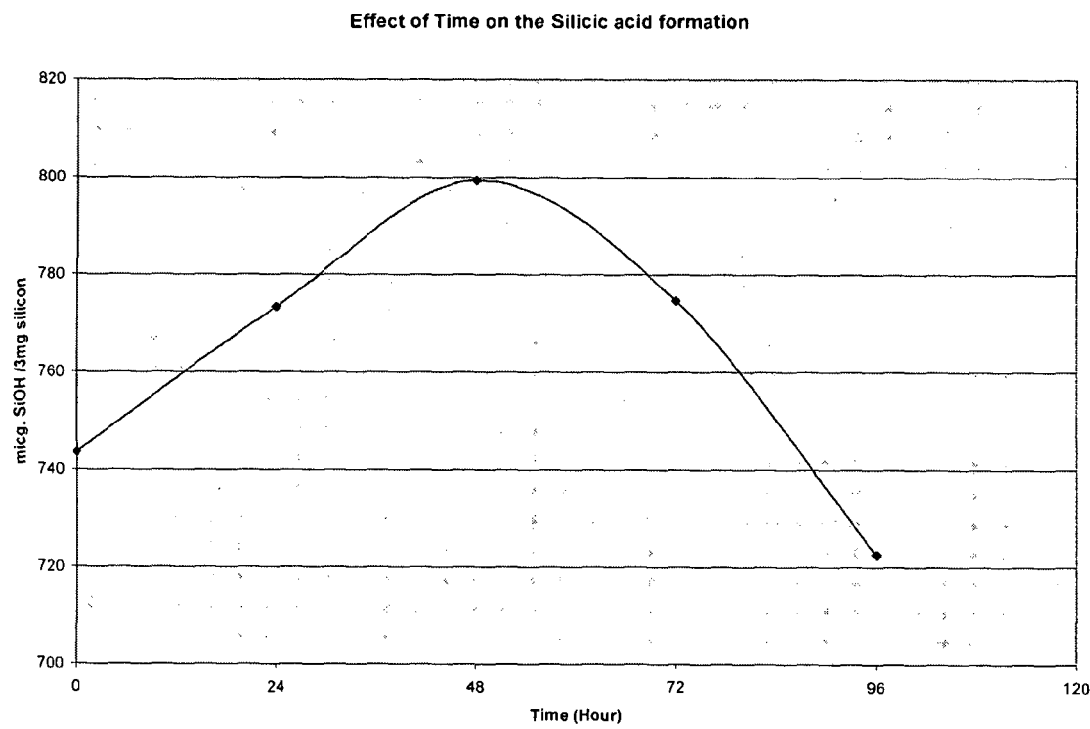
FIG. 6 shows the amounts of OSA produced from silicon nanoparticles in the absence of stabiliser over time.

Although silicon in all forms i.e. micron, nano size or porous and non porous degrades to form OSA, doesn't mean that the silicic acid remains in this form stay in this form. FIG. 6 demonstrated that although nanoparticles of silicon without surface linkage to a stabilizing agent initially degrade to form OSA, after 48 hours the level of OSA begins to decline due to polymerisation. This confirms that in order to produce OSA and avoid polymerisation of OSA you need to carefully tailor made the surface of carrier system. This data also illustrates that previous drug delivery systems using silicon or silica do not result in the production of significant levels of OSA due to polymerisation of silicic acid.

Example 6

Effect of Silicon to Stabilising Agent Ratio on OSA Production 9 mg of nano-silicon powder was collected from stock solution of activated silicon. (Silicon surface modified as described above.) Samples transfer to three universal tube, each contained 3 mg of nano particles.

Each samples contain 3 mg of Silicon formulated with different amount of active compound, Glycine. Starting amount in Tube 1 is 3 mg Si and 1.5 mg. Tube 2 contained 3 mg Si: 3 mg Glycine and tube 3 contained 3 mg Si:6 mg Glycine. Formulation made using method B as Glycine is hydrophilic amino acid.

All the samples rehydrated using 100 ml volume and left at RT for overnight. Samples subjected to centrifuges for 50 min. at 30,000 rpm. Supernatant has been collected and amount of OSA release was measured by reading the supernatant absorbance using UV spectra ($\lambda_{max}$=700 nm). Each pellet re-suspended and left at RT and the process repeated for three consecutive days. Each formulation made in triplicate. In brief 2 ml of HCl, EDTA and Molybdenum solutions were added to 7 clean and dried test tubes and left for 5 minute. 2 ml of formulation added to reagent and the amount of OSA in the solution read by UV spectra.

Figure 7:
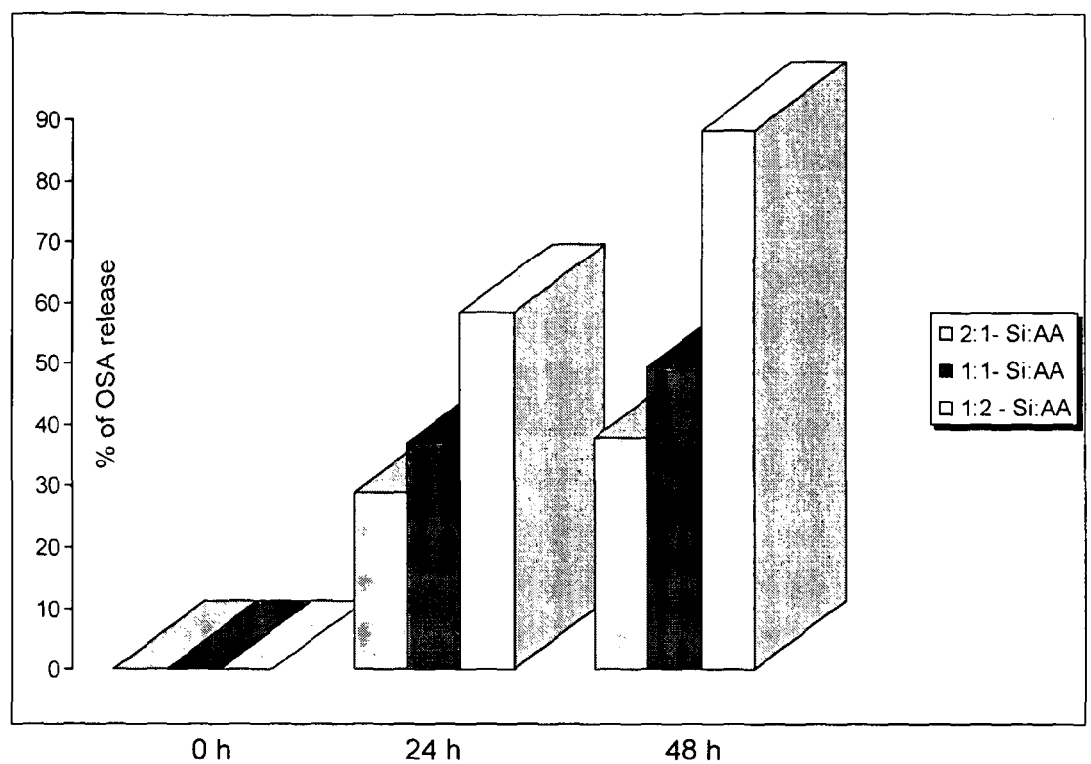
FIG. 7 shows the effect of ratio between silicon and the amino acid glycine on the production of OSA.

FIG. 7 demonstrates that the ratio of silicon to amino acid, Glycine, present in the composition has an effect on the proportion of silicic acid released as OSA. In this experiment we demonstrate the OSA production can effect by the ratio of Si:AC and the volume of media as we double the volume of the media in this study.

Example 7

Effect of Particle Size and Surface Modification with Phosphatidylcholine on OSA Formation 1 mg of surface activated nano silicon formulated with 3 mg phophatidylcholin (PC) using method A. micron silicon particles and nano silicon particles also weighed and transfer to the two other universal tubes as a control groups.

All three samples rehydrated using 50 ml volume and left at RT for overnight. Samples subjected to centrifuges for 50 min. at 30,000 rpm. Supernatant has been collected and amount of OSA release was measured by reading the supernatant absorbance using UV spectra ($\lambda_{max}$=700 nm). Each pellet re-suspended and left at RT and the process repeated for five consecutive days. Each formulation made in triplicate.

In brief 2 mL of HCl, EDTA and Molybdenum solutions were added to 7 clean and dried test tubes and left for 5 minute. 2 mL of formulation added to reagent and the amount of OSA in the solution read by UV spectra.

Figure 8:
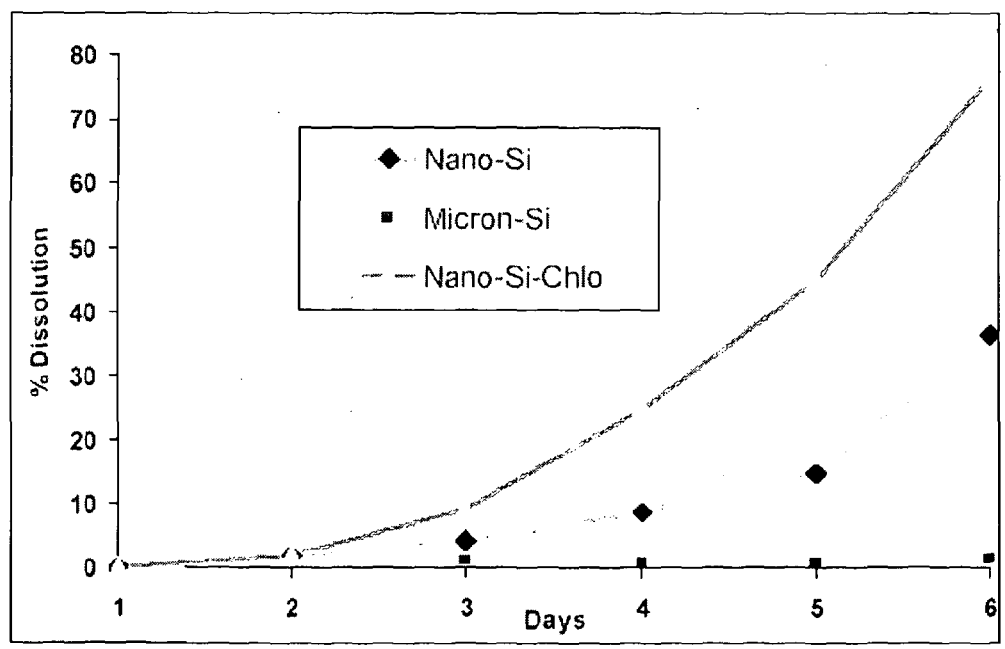
FIG. 8 shows the effect of linking the surface of a silicon nanoparticle to phosphatidylcholine on the amount of OSA produced over time.

Silicon nanoparticles were cross-linked with phosphatidylcholine molecules as described in Method C above. The amount of OSA produced upon hydrolysis over time from the surface modified particles was measured and compared with that produced from micro- and nano-sized silicon particles. The results are shown in FIG. 8. Micron size particles (around 100-500 micron) showed very little dissolution when compared with nano-silicon particles (around 10-50 nm). Nanoparticles complexed with phosphatidylcholine demonstrated further improvement in release of orthosilicic acid.

Based on our work we can clearly see the higher ratio between Silicon and Active compound/stabiliser there is better, controlled release of OSA.

The invention claimed is:

1. A composition comprising nanoparticles of a solid, hydrolysable silicon-containing semiconductor material that includes at least 50 wt % of elemental silicon for use as a delivery system for a bioactive ingredient, wherein the surface of the silicon-containing material is associated with a stabilizing agent which forms surface linkages to the silicon-containing material to (a) modify the rate of hydrolysis of the silicon-containing material, (b) stabilise orthosilicic acid in solution by inhibiting the rate of orthosilicic acid polymerisation, or (a) and (b).

2. The composition of claim 1, which is for topical application.

3. The composition of claim 1, wherein (a) the stabilizing agent is a bioactive ingredient, (b) the composition further comprises a bioactive ingredient, or (a) and (b).

4. The composition of claim 3 comprising at least 2% by weight of a bioactive ingredient.

5. The composition of claim 3 for use in therapy.

6. The composition of claim 1 for use as a cosmetic.

7. The composition of claim 1, wherein the stabilizing agent is selected from the group consisting of a quaternary ammonium compound, a compound containing a nitrogen atom with a free electron pair, an osmolyte, a monomeric sugar, an amino acid, a choline derivative, a protein or collagen hydrosylate, a polypeptide and a lipid.

8. The composition of claim 7, wherein the stabilizing agent is selected from the group consisting of a tetra-$C_{1-5}$alkyl ammonium compound, a tri-$C_{1-5}$alkyl hydroxyl-$C_{1-5}$alkyl ammonium compound, mannitol, sorbitol, lysine, proline, serine, glycine, tyrosine, aspartic acid, glutamic acid, phosphatidylcholine, albumin, collagen, retinol, retinoic acid, vitamin A, alpha-tocopherol and vitamin D.

9. The composition of claim 1, wherein the nanoparticles are silicon semiconductor particles having an average diameter of from 20 to 100 nm.

10. The composition of claim 1, wherein the composition comprises at least 1% by weight of the solid, hydrolysable silicon-containing semiconductor material.

11. The composition of claim 1, wherein the composition comprises at least 5% by weight stabilizing agent.

12. A pharmaceutical, skin care or cosmetic formulation comprising the composition of claim 1.

13. A method for the therapeutic, diagnostic or cosmetic treatment of a human or animal body comprising a step of administering to said human or animal body a composition as claimed in claim 3, said composition comprising an effective amount of the bioactive ingredient.

14. A method of promoting the controlled release of orthosilicic acid on degradation of a composition comprising nanoparticles of a solid, hydrolysable silicon-containing semiconductor material that includes at least 50 wt % of elemental silicon, said composition being suitable for use as a delivery system for a bioactive ingredient, the method involving the treatment of the surface of the silicon-containing material with a stabilizing agent, (a) which forms surface linkages to the silicon-containing material to modify the rate of hydrolysis of the silicon-containing material, (b) which stabilises orthosilicic acid in solution by inhibiting the rate of orthosilicic acid polymerisation, or (a) and (b).

15. The method of claim 14, wherein (a) the stabilizing agent is a bioactive ingredient, (b) the composition further comprises a bioactive ingredient, or (a) and (b).

16. The method of claim 15 wherein the composition comprises at least 2% by weight of a bioactive ingredient.

17. The method of claim 14, wherein the stabilizing agent is selected from the group consisting of a quaternary ammonium compound, a compound containing a nitrogen atom with a free electron pair, an osmolyte, a monomeric sugar, an amino acid, a choline derivative, a protein or collagen hydrosylate, a polypeptide and a lipid.

18. The method of claim 17, wherein the stabilizing agent is selected from the group consisting of a tetra-$C_{1-5}$alkyl ammonium compound, a tri-$C_{1-5}$alkyl hydroxyl-$C_{1-5}$alkyl ammonium compound, mannitol, sorbitol, lysine, proline, serine, glycine, tyrosine, aspartic acid, glutamic acid, phosphatidylcholine, albumin, collagen, retinol, retinoic acid, vitamin A, alpha-tocopherol and vitamin D.

19. The method of claim 14, wherein the nanoparticles are silicon semiconductor particles having an average diameter of from 20 to 100 nm.

20. The method of claim 14, wherein the composition comprises at least 1% by weight of the solid, hydrolysable silicon-containing semiconductor material.

21. The method of claim 14, wherein the composition comprises at least 30% by weight stabilizing agent.

22. The method of claim 14, wherein the rate of hydrolysis of the silicon-containing material is modified by the presence of the stabilising agent such that the rate is less than 50% of the rate of hydrolysis of an identical composition without the stabilising agent.

23. A method of preparing a solid composition for use as a delivery system for a bioactive ingredient, comprising the step of contacting nanoparticles of a solid, hydrolysable silicon-containing semiconductor material that includes at least 50 wt % of elemental silicon with a solution comprising a stabilizing agent that becomes associated with the surface of the silicon nanoparticles and removing the solvent, said stabilising agent being suitable for (a) modifying the rate of hydrolysis of the silicon by the formation of surface linkages to the silicon nanoparticles, b) inhibiting the rate of orthosilicic acid polymerisation by the stabilisation of orthosilicic acid in solution, or (a) and (b).

24. The method of claim 23 comprising the further step of impregnating the nanoparticles of a hydrolysable silicon-contain material with a bioactive ingredient either prior to or after contacting the nanoparticles with the stabilizing agent.

* * * * *